US012773097B2

(12) United States Patent
Corbeil et al.

(10) Patent No.: US 12,773,097 B2
(45) Date of Patent: Oct. 27, 2026

(54) DEVICES, SYSTEMS, AND METHODS TO SUPPLY FLUIDS TO AN ENDOSCOPE

(71) Applicant: Boston Scientific Scimed, Inc., Maple Grove, MN (US)

(72) Inventors: Scott Edward Corbeil, Litchfield, NH (US); Ryan V. Wales, Northborough, MA (US); Barry Weitzner, Acton, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 273 days.

(21) Appl. No.: 18/494,928

(22) Filed: Oct. 26, 2023

(65) Prior Publication Data

US 2024/0138663 A1 May 2, 2024

Related U.S. Application Data

(60) Provisional application No. 63/419,900, filed on Oct. 27, 2022.

(51) Int. Cl.
*A61B 1/00* (2006.01)
*A61B 1/12* (2006.01)

(52) U.S. Cl.
CPC ...... *A61B 1/00131* (2013.01); *A61B 1/00068* (2013.01); *A61B 1/00105* (2013.01); *A61B 1/00119* (2013.01); *A61B 1/126* (2013.01)

(58) Field of Classification Search
CPC ............ A61B 1/00068; A61B 1/00105; A61B 1/00119; A61B 1/00131; A61B 1/126; A61B 1/015
See application file for complete search history.

(56) References Cited

U.S. PATENT DOCUMENTS

| | | | | |
|---|---|---|---|---|
| 4,402,310 A * | 9/1983 | Kimura | A61B 1/015 604/35 |
| 5,133,336 A | 7/1992 | Savitt et al. | |
| 6,309,347 B1 * | 10/2001 | Takahashi | A61B 1/015 600/159 |
| 8,870,756 B2 | 10/2014 | Maurice | |
| 2012/0088974 A1 * | 4/2012 | Maurice | A61B 1/126 600/157 |
| 2019/0046008 A1 * | 2/2019 | Morishima | A61B 1/0055 |
| 2022/0192478 A1 | 6/2022 | Pollock et al. | |

* cited by examiner

*Primary Examiner* — Aaron B Fairchild
(74) *Attorney, Agent, or Firm* — Seager, Tufte & Wickhem, LLP

(57) ABSTRACT

Methods and systems for providing a flow of fluid to an endoscope. An illustrative container and tube set arranged and configured to couple to an endoscope may comprise, a first container configured to contain a fluid, a first water supply tube including a first lumen extending therethrough and in fluid communication with the first container, a branched connector positioned in line with first water supply tube and including a first fluid inlet, a first fluid outlet, and a second fluid outlet, a second container having a second fluid inlet in selective fluid communication with the second fluid outlet of the branched connector, a second water supply tube including a second lumen extending therethrough and in selective fluid communication with the bottom portion of the second container, and a first gas supply tube in operative fluid communication with the second container.

16 Claims, 15 Drawing Sheets

DEVICES, SYSTEMS, AND METHODS TO SUPPLY FLUIDS TO AN ENDOSCOPE

CROSS-REFERENCE TO RELATED APPLICATIONS

This application claims the benefit of U.S. Provisional Patent Application Ser. No. 63/419,900 filed on Oct. 27, 2022, the disclosure of which is incorporated herein by reference.

FIELD

This disclosure relates generally to medical fluid containers and methods, and particularly to a container and tube sets to supply fluid and/or gas to an endoscope.

BACKGROUND

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. For example, sterile water may be used to irrigate the working lumen during the procedure. Further, during endoscopic procedures, the video lens at the distal end of the endoscope, which is used to navigate and visualize target tissues, may be prone to becoming fouled with blood, mucous, and other debris during the procedure. In order to reduce complications that may arise from removing the endoscope, manually cleaning the lens, and re-inserting (such as trauma or infection) nearly all endoscopes may be equipped with a lumen through which a cleaning fluid (which may typically be sterile water) can be delivered to the surface of the lens for the purpose of de-fouling.

The current state of the art for devices used to deliver sterile water to the endoscope for the purpose of irrigation and endoscope lens washing draw and/or push water from either one or two disposable bottles of sterile water (typically 1 L volume). In the two-bottle system, two separate disposable sterile water bottles may be used to supply sterile water separately to the endoscope for irrigation or lens washing. For irrigation, a flexible conduit may extend through a cap, which can be fitted onto the sterile water bottle after opening, and to the bottom of the bottle on the inlet end, may be inserted within the drive head of a peristaltic roller pump and connected to the endoscope through a scope specific connector. In the two-bottle system, a second sterile water bottle may be fitted with a cap having an inlet tube/connector which allows pressurized air or $CO_2$ gas to enter the bottle, and having a flexible conduit which extends from the bottle to, and connecting with, the lens wash port of the endoscope via a scope specific connector. Using this system, $CO_2$ gas may be supplied to the bottle at a pre-determined pressure, which in turn creates a pressure differential, driving sterile water through the conduit to the lens wash inlet of the endoscope, such that when the lens wash switch on the endoscope is triggered, sterile water jets through a dedicated lumen within the endoscope and washes sterile water over the fouled lens, thus clearing the lens.

In the one-bottle system, a cap may be attached to a single water bottle having a first conduit extending to the bottom of the bottle and extends through the roller pump and connecting to the irrigation port of the endoscope. A second conduit may extend to the bottom of the bottle and extend to the lens wash port on the endoscope. A third conduit may bring pressurized gas (e.g., air or $CO_2$) into the bottle through a port on the cap. This system may allow a single sterile water bottle to be used for both lens wash and irrigation instead of a separate bottle for lens wash and irrigation.

Currently commercialized systems for delivering sterile water to the endoscope may rely on commercially available bottles of sterile water, with which the sterile water is pumped or pushed with compressed gas from the bottle to the scope. The volume of water available to the user is limited by the size/volume of commercially available sterile water bottles and space on procedure carts. In many hospital centers, the sterile water delivery systems may have a one-way valve at the end of the conduit to the scope to prevent backflow of fluids from the patient end of the scope back to the inlet sterile water conduit so that the sterile water delivery system may be used for multiple cases, over the course of a day.

As clinicians work through each case some volume of water is depleted from the water bottle and bottles may need to be replaced one or more times over the course of the day. The process of exchanging bottles may require the user to bend or stoop down, remove the cap and associated inlet tubes from the empty bottle, and place them into a full bottle of sterile water without touching/contaminating the tubes against the external bottle or other non-sterile surfaces (e.g., so as not to create an infection risk to the patient). This may be especially difficult in the single bottle devices where multiple inlet hoses dangle from the cap when removing the cap to replace the sterile water bottle.

Additionally, having the sterile water bottles stowed on lower shelves of the carts, alongside the peristaltic pump, and other equipment may make these difficult to visualize and often, the clinician may not realize that the bottle is nearing empty until they are no longer able to deliver irrigation or lens wash to the distal end of the scope. There is also an inherent risk associated with stowing the water bottles adjacent to the endoscope control boxes. For example, if the water bottle fails in some way (e.g., leak, burst, rupture, etc.) there may be a high risk of water running or spraying onto these high-cost control systems resulting in significant damage or destruction. It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, a container and tube set arranged and configured to couple to an endoscope for use in an endoscopic procedure may comprise a first container configured to contain a fluid, the first container having a port in fluid communication with a bottom portion thereof, a first water supply tube including a first end, a second end, and a first lumen extending therethrough, wherein the first lumen is in fluid communication with the first container and the second end of the first water supply tube is positioned external to the first container, a branched connector positioned in line with the first water supply tube between the first and second ends thereof, the branched connector including a first fluid inlet, a first fluid outlet, and a second fluid outlet, a portion of the first lumen of the first water supply tube extending between the first fluid inlet and the first fluid outlet, a second container configured to contain a fluid, the second container having a second fluid inlet in selective fluid communication with the second fluid outlet of the branched connector, a second water supply tube including a first end, a second end, and a second lumen extending therethrough, wherein the second lumen is in selective fluid communication with the bottom portion of the second container and the second end of the second water supply tube is positioned external to the second container, and a first gas supply tube including a first end, a second end, and a third lumen extending therethrough, wherein the third lumen is in operative fluid communication with the second container and the second end of the first gas supply tube is positioned external to the second container.

Alternatively or additionally to any of the examples above, in another example, the first container may comprise a collapsible bag.

Alternatively or additionally to any of the examples above, in another example, the first container may comprise a rigid bottle.

Alternatively or additionally to any of the examples above, in another example, the rigid bottle may comprise a vented cap.

Alternatively or additionally to any of the examples above, in another example, the second container may comprise a collapsible bag.

Alternatively or additionally to any of the examples above, in another example, the second container may comprise a rigid bottle.

Alternatively or additionally to any of the examples above, in another example, the branched connector may be selected from a “Y” connector and a “T” connector.

Alternatively or additionally to any of the examples above, in another example, the container and tube set may further comprise a one-way valve positioned between the second fluid outlet of the branched connector and the second fluid inlet of the second container.

Alternatively or additionally to any of the examples above, in another example, the one-way valve may be configured to selectively fluidly couple the first container with the second container.

Alternatively or additionally to any of the examples above, in another example, the one-way valve may be configured to preclude a flow of fluid from the second container to the first container.

Alternatively or additionally to any of the examples above, in another example, the container and tube set may further comprise a valve positioned between the second fluid outlet of the branched connector and the second fluid inlet of the second container.

Alternatively or additionally to any of the examples above, in another example, the valve may be configured to selectively fluidly couple the first container with the second container.

Alternatively or additionally to any of the examples above, in another example, the valve may be configured to preclude a flow of fluid from the second container to the first container.

Alternatively or additionally to any of the examples above, in another example, the container and tube set may further comprise a second gas supply tube including a first end, a second end, and a fourth lumen extending therethrough. The fourth lumen may be in operative fluid communication with the second container and the second end of the second gas supply tube may be positioned external to the second container.

Alternatively or additionally to any of the examples above, in another example, the first end of the second water supply tube may be fluidly coupled to a bottom portion of the second container.

Alternatively or additionally to any of the examples above, in another example, the first end of the first gas supply tube may be fluidly coupled to a bottom portion of the second container.

Alternatively or additionally to any of the examples above, in another example, the container and tube set may further comprise a flow control valve in line with the first water supply line adjacent the second end thereof.

Alternatively or additionally to any of the examples above, in another example, the container and tube set may further comprise a manifold coupled to the first end of the first water supply tube.

Alternatively or additionally to any of the examples above, in another example, the manifold may include a plurality of fluid inlets each configured to be coupled to a fluid container and a third fluid outlet. At least one of the plurality of fluid inlets may be fluidly coupled with the first container and the third fluid outlet may be fluidly coupled to the first water supply tube.

In another example, a container and tube set arranged and configured to couple to an endoscope for use in an endoscopic procedure may comprise a first container configured to contain a fluid, the first container having a port in fluid communication with a bottom portion thereof, a first water supply tube including a first end, a second end, and a first lumen extending therethrough, wherein the first lumen is in fluid communication with the first container and the second end of the first water supply tube is positioned external to the first container, a branched connector positioned in line with the first water supply tube between the first and second ends thereof, the branched connector including a first fluid inlet, a first fluid outlet, and a second fluid outlet, a portion of the first lumen of the first water supply tube extending between the first fluid inlet and the first fluid outlet, a second container configured to contain a fluid, the second container having a second fluid inlet in selective fluid communication with the second fluid outlet of the branched connector, a second water supply tube including a first end, a second end, and a second lumen extending therethrough, wherein the second lumen is in selective fluid communication with the bottom portion of the second container and the second end of the second water supply tube is positioned external to the second container, and a first gas supply tube including a first end, a second end, and a third lumen extending therethrough, wherein the third lumen is in operative fluid communication with the second container and the second end of the first gas supply tube is positioned external to the second container.

Alternatively or additionally to any of the examples above, in another example, the first and second containers may each comprise a collapsible bag.

Alternatively or additionally to any of the examples above, in another example, the first and second containers may each comprise a rigid bottle.

Alternatively or additionally to any of the examples above, in another example, the first container may comprise a vented cap or a vented spike port cap.

Alternatively or additionally to any of the examples above, in another example, the container and tube set may further comprise a one-way valve positioned between the second fluid outlet of the branched and the second fluid inlet of the second container.

Alternatively or additionally to any of the examples above, in another example, the one-way valve may be configured to selectively fluidly couple the first container with the second container.

Alternatively or additionally to any of the examples above, in another example, the one-way valve may be configured to preclude a flow of fluid from the second container to the first container.

Alternatively or additionally to any of the examples above, in another example, the container and tube set may further comprise a second gas supply tube including a first end, a second end, and a fourth lumen extending therethrough. The fourth lumen may be in operative fluid communication with the second container and the second end of the first gas supply tube may be positioned external to the second container.

Alternatively or additionally to any of the examples above, in another example, the first ends of the second water supply tube and the first gas supply tube are fluidly coupled to a bottom portion of the second container.

Alternatively or additionally to any of the examples above, in another example, the container and tube set may further comprise a flow control valve in line with the first water supply line adjacent the second end thereof.

Alternatively or additionally to any of the examples above, in another example, the container and tube set may further comprise a manifold coupled to the first end of the first water supply tube.

Alternatively or additionally to any of the examples above, in another example, the manifold may include a plurality of fluid inlets each configured to be coupled to a fluid container and a third fluid outlet. At least one of the plurality of fluid inlets may be fluidly coupled with the first container and the third fluid outlet may be fluidly coupled to the first water supply tube.

In another example, a container and tube set arranged and configured to couple to an endoscope for use in an endoscopic procedure may comprise a first container configured to contain a fluid, the first container having a port in fluid communication with a bottom portion thereof, a first water supply tube including a first end, a second end, and a first lumen extending therethrough, wherein the first lumen is in fluid communication with the first container and the second end of the first water supply tube is positioned external to the first container, a branched connector positioned in line with first water supply tube between the first and second ends thereof, the branched connector including a first fluid inlet, a first fluid outlet, and a second fluid outlet, a portion of the first lumen of the first water supply tube extending between the first fluid inlet and the first fluid outlet, a second container configured to contain a fluid, the second container having a second fluid inlet in selective fluid communication with the second fluid outlet of the branched connector, a one-way valve positioned between the second fluid outlet of the branched connector and the second fluid inlet of the second container, a second water supply tube including a first end, a second end, and a second lumen extending therethrough, wherein the second lumen is in selective fluid communication with the bottom portion of the second container and the second end of the second water supply tube is positioned external to the container, a first gas supply tube including a first end, a second end, and a third lumen extending therethrough, wherein the third lumen is in operative fluid communication with the second container and the second end of the first gas supply tube is positioned external to the second container, and a second gas supply tube including a first end, a second end, and a fourth lumen extending therethrough, wherein the fourth lumen is in operative fluid communication with the second container and the second end of the first gas supply tube is positioned external to the second container.

Alternatively or additionally to any of the examples above, in another example, the container and tube set may further comprise a manifold coupled to the first end of the first water supply tube.

Alternatively or additionally to any of the examples above, in another example, the manifold may include a plurality of fluid inlets each configured to be coupled to a fluid container and a third fluid outlet. At least one of the plurality of fluid inlets may be fluidly coupled with the first container and the third fluid outlet may be fluidly coupled to the first water supply tube.

Alternatively or additionally to any of the examples above, in another example, the first and second containers may each comprise a collapsible bag.

In another example, a manifold assembly for use with a container and tube set arranged and configured to couple to an endoscope for use in an endoscopic procedure may comprise a housing comprising two or more fluid inlets and a fluid outlet in fluid communication with the two or more fluid inlets, a fluid tube coupled to each of the two or more fluid inlets, and a spike port positioned at an inlet end of each of the fluid tubes.

Alternatively or additionally to any of the examples above, in another example, each fluid inlet of the two or more fluid inlets may be configured to be fluidly coupled with a separate fluid container.

Alternatively or additionally to any of the examples above, in another example, each fluid tube may comprise a removable clamp.

Alternatively or additionally to any of the examples above, in another example, the fluid outlet may be configured to be in fluid communication with an irrigation and/or lens wash circuit of an endoscope.

Alternatively or additionally to any of the examples above, in another example, each spike port may be configured to form an interference fit with the port of the container.

In another example, a container and tube set arranged and configured to couple to an endoscope for use in an endoscopic procedure may comprise a container configured to contain a fluid, the first container having a port in fluid communication with a bottom portion thereof, a water supply tube including a first end, a second end, and a first lumen extending therethrough, wherein the first lumen is in fluid communication with the first container and the second end of the first water supply tube is positioned external to the first container, and a flow control valve in line with the first water supply line adjacent the second end thereof. The container may comprise a flexible bag.

Alternatively or additionally to any of the examples above, in another example, the second end of the water supply tube may be configured to be fluidly coupled with an irrigation lumen of an endoscope.

Alternatively or additionally to any of the examples above, in another example, the first end of the water supply tube may comprise a spike port.

Alternatively or additionally to any of the examples above, in another example, the spike port may be configured to form an interference fit with the port of the container.

In another example, a container and tube set arranged and configured to couple to an endoscope for use in an endoscopic procedure may comprise a first container configured to contain a fluid, the first container having a port in fluid communication with a bottom portion thereof, a second container configured to contain a fluid, the second container including a partition positioned within an interior thereof, the partition dividing the second container into a first sub-chamber and a second sub-chamber, a first water supply tube including a first end, a second end, and a first lumen extending therethrough, wherein the first lumen is in fluid communication with the first container and the second container, a second water supply tube including a first end, a second end, and a second lumen extending therethrough, wherein the second lumen is in selective fluid communication with a bottom portion of the second sub-chamber of the second container and the second end of the second water supply tube is positioned external to the second container, a first gas supply tube including a first end, a second end, and a third lumen extending therethrough, wherein the third lumen is in operative fluid communication with the second sub-chamber of the second container and the second end of the first gas supply tube is positioned external to the second container, and a third water supply tube including a first end, a second end, and a fourth lumen extending therethrough, wherein the fourth lumen is in selective fluid communication with a bottom portion of the first sub-chamber of the second container and the second end of the second water supply tube is positioned external to the second container.

Alternatively or additionally to any of the examples above, in another example, the second container may further comprise a port positioned adjacent to a top portion thereof.

Alternatively or additionally to any of the examples above, in another example, the container and tube set may further comprise a cap configured to be releasably coupled to the port, the cap configured to selectively fluidly couple the first and second sub-chambers.

Alternatively or additionally to any of the examples above, in another example, the second end of the first water supply tube may be coupled with the cap.

Alternatively or additionally to any of the examples above, in another example, the cap may be configured to allow of flow of fluid through the first lumen of the first water supply tube into the first and second sub-chambers.

Alternatively or additionally to any of the examples above, in another example, the cap may further comprise a one-way valve. The one-way valve may be configured to allow a flow of fluid into the second sub-chamber and preclude a flow of fluid from the second sub-chamber to the first sub-chamber.

Alternatively or additionally to any of the examples above, in another example, the container and tube set may further comprise a second gas supply tube including a first end, a second end, and a fifth lumen extending therethrough. The fifth lumen may be in operative fluid communication with the second sub-chamber of the second container and the second end of the second gas supply tube may be positioned external to the second container.

Alternatively or additionally to any of the examples above, in another example, the first container may comprise a collapsible bag.

Alternatively or additionally to any of the examples above, in another example, the first container may comprise a rigid bottle.

Alternatively or additionally to any of the examples above, in another example, the second container may comprise a collapsible bag.

Alternatively or additionally to any of the examples above, in another example, the second container may comprise a rigid bottle.

In another example, a container and tube set arranged and configured to couple to an endoscope for use in an endoscopic procedure may comprise a container configured to contain a fluid, the first container having a port in fluid communication with a bottom portion thereof, a fluid connection tube including a first end, a second end, a first lumen and a second lumen extending therethrough, wherein the first lumen is in fluid communication with the container, a first water supply tube including a first end, a second end, and a third lumen extending therethrough, a first gas supply tube including a first end, a second end, and a fourth lumen extending therethrough, and a manifold including a first end fluidly coupled to the second end of the fluid connection tube and a second end fluidly coupled to the first water supply tube and the first gas supply tube, the manifold configured to fluidly couple the first lumen of the fluid connection tube with the third lumen of the first water supply tube and the second lumen of the fluid connection tube with the fourth lumen of the first gas supply tube.

Alternatively or additionally to any of the examples above, in another example, the container and tube set may further comprise a spike port coupled to the first end of the fluid connection tube.

Alternatively or additionally to any of the examples above, in another example, the spike port may be configured to frictionally engage the port of the container.

Alternatively or additionally to any of the examples above, in another example, the first lumen may extend co-axially within the second lumen.

Alternatively or additionally to any of the examples above, in another example, the first lumen may extend side-by-side with the second lumen.

Alternatively or additionally to any of the examples above, in another example, the container and tube set may further comprise a second water supply tube including a first end, a second end, and a fifth lumen extending therethrough.

Alternatively or additionally to any of the examples above, in another example, the first end of the second water supply tube may be fluidly coupled to a second end of the manifold. The manifold may be configured to fluidly couple the fifth lumen of the second water supply tube with the first lumen of the fluid connection tube.

Alternatively or additionally to any of the examples above, in another example, the container and tube set may further comprise a second gas supply tube including a first end, a second end, and a sixth lumen extending therethrough.

Alternatively or additionally to any of the examples above, in another example, the first end of the second gas supply tube may be fluidly coupled to a second end of the manifold, the manifold configured to fluidly couple the sixth lumen of the second gas supply tube with the second lumen of the fluid connection tube.

In another example, a container and tube set arranged and configured to couple to an endoscope for use in an endoscopic procedure may comprise a first container configured to contain a fluid, the first container having a port in fluid communication with a bottom portion thereof, a first water supply tube including a first end, a second end, and a first lumen extending therethrough, wherein the first lumen is in fluid communication with the first container and the second end of the first water supply tube is positioned external to the first container, a branched connector positioned in line with first water supply tube between the first and second ends thereof, the branched connector including a first fluid inlet, a first fluid outlet, and a second fluid outlet, a second container configured to contain a fluid, the second container having a second fluid inlet in selective fluid communication with the first fluid outlet of the branched connector, and a third container configured to contain a fluid, the third container having a third fluid inlet in selective fluid communication with the second fluid outlet of the branched connector.

Alternatively or additionally to any of the examples above, in another example, the container and tube set may further comprise a second water supply tube including a first end, a second end, and a second lumen extending therethrough. The second lumen may be in selective fluid communication with the bottom portion of the second container and the second end of the second water supply tube may be positioned external to the second container.

Alternatively or additionally to any of the examples above, in another example, the container and tube set may further comprise a third water supply tube including a first end, a second end, and a third lumen extending therethrough and a first gas supply tube including a first end, a second end, and a fourth lumen extending therethrough. The third lumen may be in selective fluid communication with the bottom portion of the third container and the second end of the third water supply tube may be positioned external to the third container. The fourth lumen may be in operative fluid communication with the third container and the second end of the first gas supply tube may be positioned external to the third container.

Alternatively or additionally to any of the examples above, in another example, the container and tube set may further comprise a second gas supply tube including a first end, a second end, and a fifth lumen extending therethrough. The fifth lumen may be in operative fluid communication with the third container and the second end of the first gas supply tube may be positioned external to the third container.

Alternatively or additionally to any of the examples above, in another example, the container and tube set may further comprise a first fluid connection tube extending between the first fluid outlet of the branched connector and the second container.

Alternatively or additionally to any of the examples above, in another example, the container and tube set may further comprise a second fluid connection tube extending between the second fluid outlet of the branched connector and the third container.

Alternatively or additionally to any of the examples above, in another example, the container and tube set may further comprise a releasable clamp disposed about the second fluid connection tube.

Alternatively or additionally to any of the examples above, in another example, the releasable clamp may be movable between an open configuration configured to allow fluid flow through the second fluid connection tube and a closed configuration configured to fluidly isolate the third container from the first container.

In another example, a container and tube set arranged and configured to couple to an endoscope for use in an endoscopic procedure may comprise a first container configured to contain a fluid, the first container having a port in fluid communication with a bottom portion thereof, a water supply tube including a first end, a second end, and a first lumen extending therethrough, wherein the first lumen is in fluid communication with the first container and the second end of the first water supply tube is positioned external to the first container, a first flow control valve in line with the first water supply line adjacent the second end thereof, and a second container fluidly coupled to an outlet of the first flow control valve via a three-way port, the second container including a pressure control device fluidly coupled to a top portion of the second container.

Alternatively or additionally to any of the examples above, in another example, the pressure control device may comprise a plunger.

Alternatively or additionally to any of the examples above, in another example, the pressure control device may comprise a bellows mechanism.

Alternatively or additionally to any of the examples above, in another example, the container and tube set may further comprise a biasing mechanism configured to bias the pressure control device to a first configuration.

Alternatively or additionally to any of the examples above, in another example, the biasing mechanism may comprise a spring.

Alternatively or additionally to any of the examples above, in another example, the container and tube set may further comprise a second flow control valve positioned adjacent to an outlet of the three-way port.

Alternatively or additionally to any of the examples above, in another example, when an interior of the second container is free from fluid, actuation of the pressure control device may be configured to pull fluid into the interior of the second container from the first container.

Alternatively or additionally to any of the examples above, in another example, when an interior of the second container includes a fluid, actuation of the pressure control device may be configured to expel fluid from the interior of the second container and through an outlet of the three-way port.

Alternatively or additionally to any of the examples above, in another example, the pressure control device may be configured to return to a first orientation after expulsion of the fluid and the return of the pressure control device to the first orientation may be configured to pull fluid into the interior of the second container from the first container.

Alternatively or additionally to any of the examples above, in another example, a quantity of fluid expelled from the interior of the second container may be directly correlated to a degree of actuation of the pressure control device.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
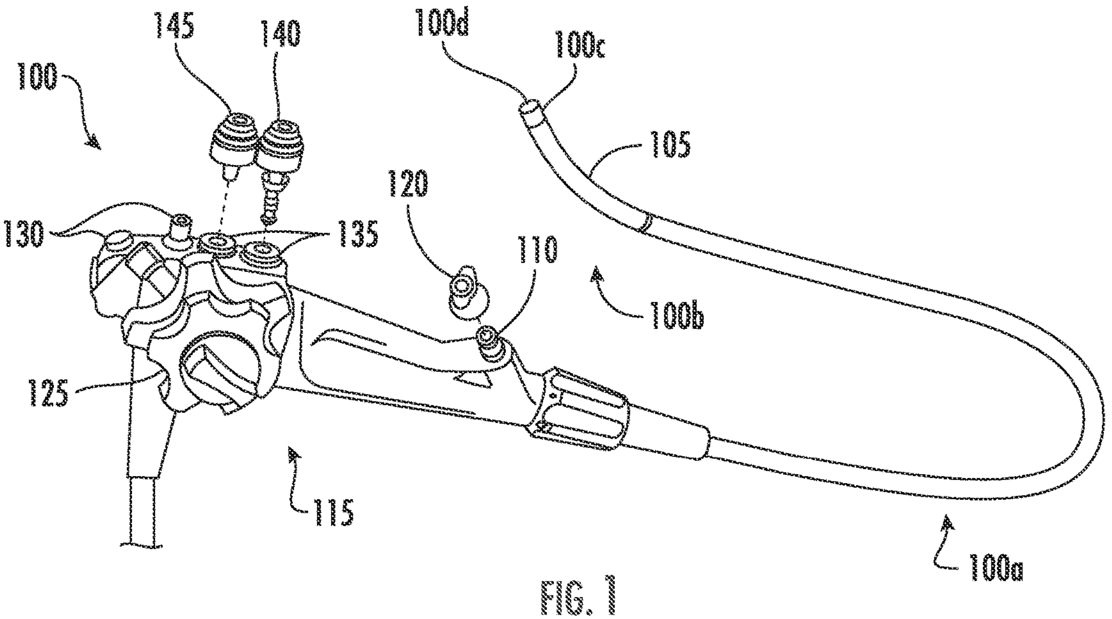
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure are described with specific reference to a bottle (e.g., container, reservoir, or the like) and tube assembly or set. It should be appreciated that such embodiments may be used to supply fluid and/or gas to an endoscope, for a variety of different purposes, including, for example to facilitate insufflation of a patient, lens washing, and/or to irrigate a working channel to aid in flushing/suctioning debris during an endoscopic procedure.

Although the present disclosure includes descriptions of a container and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. Some systems may use two separate water bottles for irrigation and lens wash while other systems may use a single water bottle for both irrigation and lens wash. As clinicians work through each case, some volume of water is depleted from the water bottle and bottles may need to be replaced one or more times over the course of the day. The process of exchanging bottles may require the user to bend or stoop down, remove the cap and associated inlet tubes from the empty bottle, and place them into a full bottle of sterile water without touching/contaminating the tubes against the external bottle or other non-sterile surfaces (e.g., so as not to create an infection risk to the patient). This may be especially difficult in the single bottle devices where multiple inlet hoses dangle from the cap when removing the cap to replace the sterile water bottle.

Additionally, having the sterile water bottles stowed on lower shelves of the carts, alongside the peristaltic pump, and other equipment may make these difficult to visualize and often, the clinician may not realize that the bottle is nearing empty until they are no longer able to deliver irrigation or lens wash to through the distal end of the scope. There is also an inherent risk associated with stowing the water bottles adjacent to the endoscope control boxes. For example, if the water bottle fails in some way (e.g., leak, burst, rupture, etc.) there may be a high risk of water running or spraying onto these high-cost control systems resulting in significant damage or destruction. Disclosed herein are containers and tube sets that are easily viewed by the clinician and reduces the risk of contamination to the tubes when the container is replaced.

Figure 2:
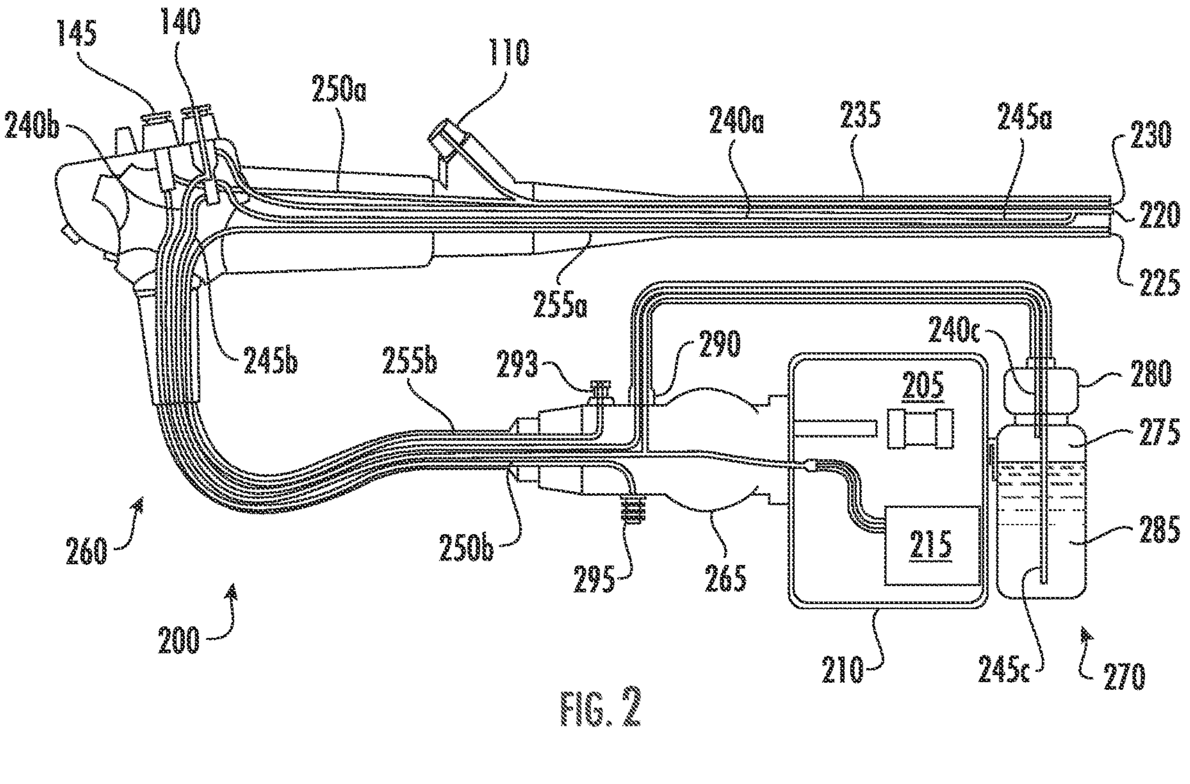
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100*a* that is inserted into a patient. A light source 205 feeds illumination light to a distal portion 100*b* of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100*a* may include a distal tip 100*c* provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 extends along the shaft 100*a* to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2). The other valve well 135 receives a suction valve 145 for operating a suction operation. A suction supply line 250*a* runs distally from the suction valve 145 along the shaft 100*a* to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) is fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240*c*. The gas feed line 240*b* from the umbilical 260 branches in the connector portion 265 to fluidly communicate with the gas supply tubing 240*c* at the detachable gas/lens wash connection 290, as well as the air pump 215. A length of lens wash tubing 245*c*, with one end positioned at the bottom of the reservoir 270, passes through the top 280 of the reservoir 270 to the same detachable connection 290 as the gas supply tubing 240*c* on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255*b* in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100. The detachable suction connection 295 may be detachable from the connector portion 265 and/or the suction feed line 250*b* and/or the vacuum source.

The gas feed line 240*b* and lens wash feed line 245*b* are fluidly connected to the valve well 135 for the gas/water valve 140 and configured such that operation of the gas/water valve 140 in the well controls supply of gas or lens wash to the distal tip 100*c* of the endoscope 100. The suction feed line 250*b* is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240*b* in the umbilical 260, as well as through the gas supply tubing 240*c* to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240*a* and out the distal tip 100*c* of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245*c*, through the connector portion 265, umbilical 260, through the gas/water valve 140 and down the lens wash supply line 245*a*, converging with the gas supply line 240*a* prior to exiting the distal tip 100*c* of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245*c*, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240*c* to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255*b* in the umbilical 260 and the irrigation supply line 255*a* endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255*b* in the umbilical, and down the irrigation supply line in the shaft 100*a* of the endoscope to the distal tip 100*c*. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245*c*, may be placed in the path of the irrigation supply tubing to help prevent back-flow into the reservoir after water has passed the valve.

FIGS. 3A-3D are schematic drawings illustrating the operation of an embodiment of a hybrid system 300 where the supply tubing for irrigation and lens wash are connected to and drawn from a single water reservoir. It is contemplated that fluids other than water may be used, such as, but not limited to saline. The hybrid system 300 includes the single water reservoir 305, a cap 310 for the reservoir, gas supply tubing 240*c*, lens wash supply tubing 245*c*, irrigation pump 315 with foot switch 318, upstream supply tubing for irrigation 320 and downstream irrigation supply tubing 255*c*. The cap 310 may be configured to attach in a seal-tight manner to the water reservoir 305 by a typically threaded arrangement. The cap 310 may include a gasket to seal the cap 310 to the reservoir 305. The gasket can be an O-ring, flange, collar, and/or the like and can be formed of any suitable material. A number of through-openings (325*a*, 325*b*, 325*c*) in the cap 310 are provided to receive, respectively, the gas supply tubing 240*c*, lens wash supply tubing 245*c*, and upstream irrigation supply tubing 320. In FIGS. 3A-3D, the system depicted includes separate tubing for gas supply, lens wash, and irrigation.

In other embodiments, the gas supply tubing 240*c* and lens wash tubing 245*c* may be combined in a coaxial arrangement. Some illustrative coaxial arrangements are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference. For example, the gas supply tubing may define a lumen that is sufficiently large in diameter to encompass a smaller diameter lens wash tubing, coaxially received within the gas supply tubing, as well as provide air to the water source in an annular space surrounding the lens wash tubing to pressurize the water reservoir (see, e.g., gas and lens wash supply tubing 240*c*, 245*c*). The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2).

In various embodiments, different configurations of valving (not shown) may be incorporated into various embodiments disclosed hereby, including the tubing of the system 200, 300. For example, an in-flow check valve can be disposed in the path of the gas supply tubing 240*c* to help prevent backflow into the air pump 215. In this manner, pressure building within the water reservoir 305 creates a pressure difference between the water source and the gas supply tubing 240*c* helping to maintain a positive pressure in the water source even when large amounts of water may be removed from the water source during the irrigation function. This arrangement compensates for any time lag in air being delivered from the air pump 215 to the water reservoir 305, which might otherwise cause a negative pressure vacuum in the water reservoir. Similarly, an outflow check valve, such as the one-way valve with inlet/outlets and valve insert, may be incorporated in the lens wash supply tubing 245*c*, upstream irrigation supply tubing 320, and/or downstream irrigation supply tubing 255*c* to help prevent backflow of water from either or both of the lens wash and supply tubing for irrigation in the event of a negative pressure situation, as described.

More generally, in many embodiments, a check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, a flow check. Accordingly, a check valve as used herein is meant to be separate and distinct from an active valve that is operated in a binary manner as an on/off valve or switch to allowed flow to be turned on or allow flow to be turned off (e.g., a stop cock valve, solenoid valve, peristaltic pump).

During operation of the system of FIGS. 3A-3D, a flow of water for irrigation may be achieved by operating the irrigation pump 315. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 305, the pressure in the system may be controlled to maintain the lens wash supply tubing 245*c* at substantially the pressure necessary to accomplish a lower flow rate lens wash, while compensating for reduced pressure in the water reservoir 305 due to supplying a high flow rate irrigation. When pressure is reduced in the water reservoir by use of the lens wash function, the irrigation function, or both functions simultaneously, the reduced pressure may be compensated for by the air pump 215 via the gas supply tubing 240*c*.

Figure 3A:
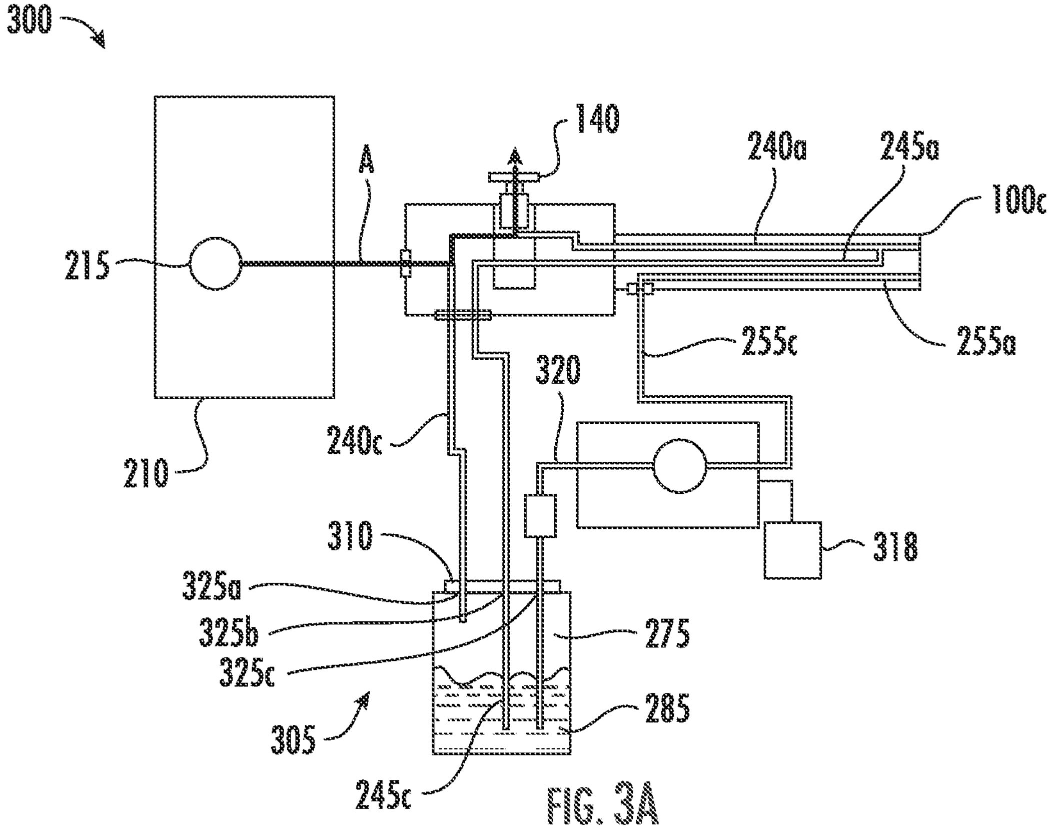
FIG. 3A depicts an endoscope system with endoscope, light source, water reservoir, and tubing assembly for hybrid air, lens wash and irrigation fluid delivery, wherein the system is activated to deliver air to atmosphere.

The schematic set-up in FIGS. 3A-3D has been highlighted to show the different flow paths possible with the hybrid system 300 having supply tubing for irrigation 320 and lens wash supply tubing 245*c* connected to and drawn from the single water reservoir 305. As shown in FIG. 3A, the endoscope 100 is in a neutral state with the gas/water valve 140 in an open position. The neutral state delivers neither gas, nor lens wash, to the distal tip of the endoscope. Rather gas (pressure) is delivered along path A from the pressurizing air pump 215 and vented through the gas feed line 240*b* in the umbilical 260 via the connector portion 265 and through the gas/water valve to atmosphere. Since the system is open at the vent hole in the gas/water valve 140, there is no build up to pressurize the water reservoir 305 and consequently no water is pushed through the lens wash supply tubing 245*c*.

Figure 3B:
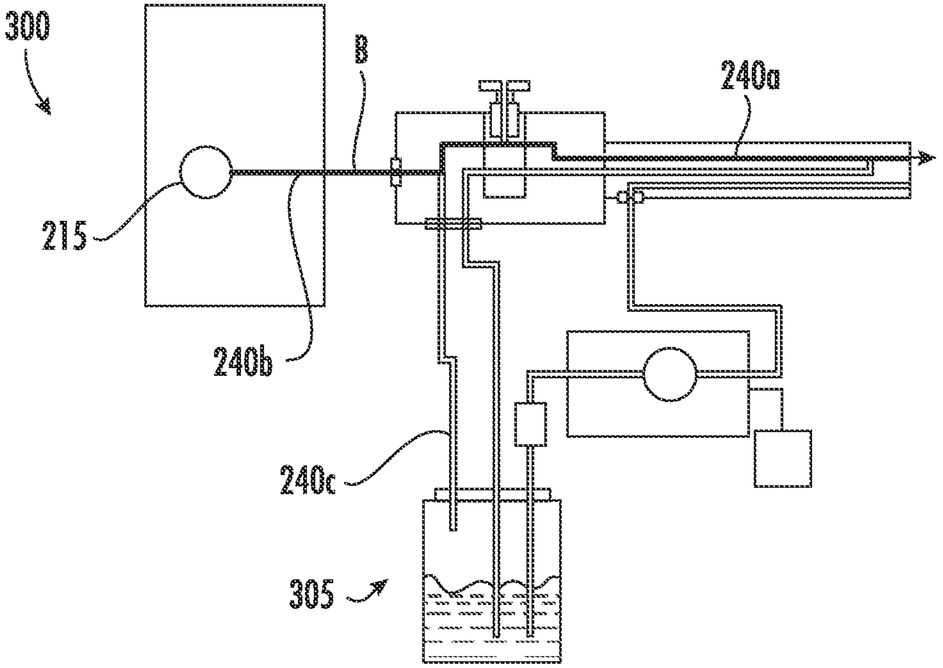
FIG. 3B depicts the endoscope system of FIG. 3A, wherein the system is activated to deliver air to a patient through the patient end of the endoscope.

As shown in FIG. 3B, the endoscope 100 is in a gas delivery state with the gas/water valve 140 in a first position. When gas is called for at the distal tip 100*c*, for example, to clean the end face 100*d* of the distal tip or insufflate the patient body in the treatment area, the user closes off the vent hole in the gas/water valve 140 with a thumb, finger, or the like (first position). In this state, gas (pressure) is delivered along path B from the air pump 215 and flowed through the gas feed line 240*b* in the umbilical 260 via the connector portion 265. The gas continues through the gas/water valve 140 to the gas supply line 240*a* in the endoscope shaft 100*a* and out the gas/lens wash nozzle 220 at the distal tip 100*c*. There is no build up to pressurize the water reservoir since the system is open at the gas/lens water nozzle 220, and consequently no water is pushed through the lens wash supply tubing 245*c*.

Figure 3C:
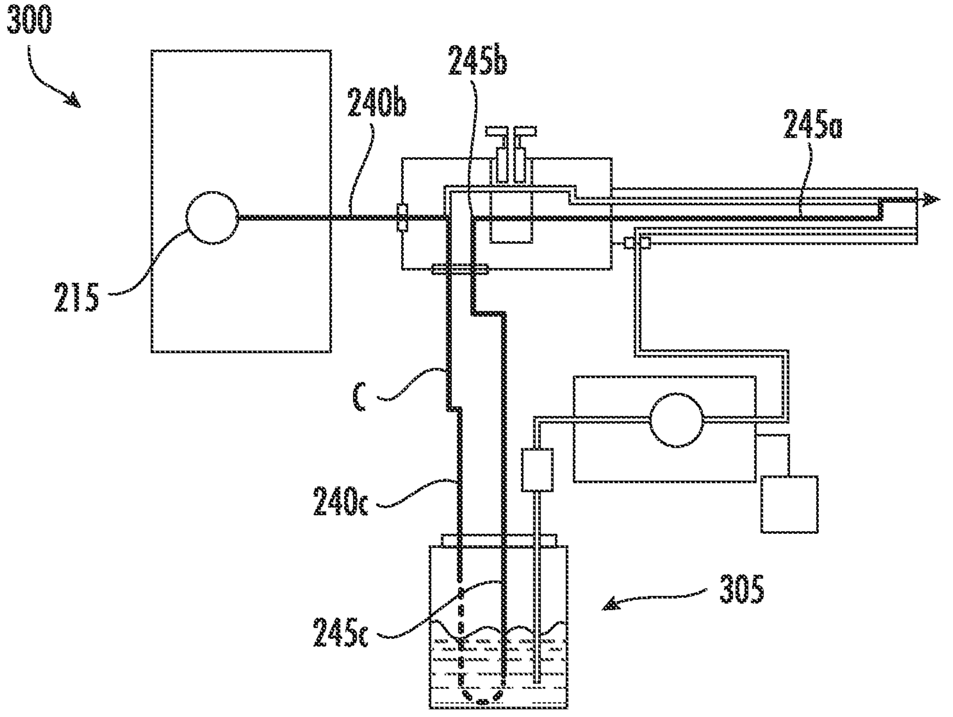
FIG. 3C depicts the endoscope system of FIG. 3A, wherein the system is activated to deliver lens wash fluid through the patient end of the endoscope.

As shown in FIG. 3C, the endoscope 100 is in a lens wash delivery state with the gas/water valve 140 in a second position. When lens wash is called for at the distal tip 100*c*, for example, to clean the end face 100*d* of the distal tip 100*c*, the user, keeping the vent hole in the air/water valve closed off, depresses the valve 140 to its furthest point in the valve well 135. The second position blocks off the gas supply to both atmosphere and the gas supply line 240*a* in the endoscope, and opens up the gas/water valve 140 to allow lens wash water to pass through to the lens wash supply line 245*a* in the endoscope shaft 100*a* and out the gas/lens wash nozzle 220 at the distal tip 100*c*. In this state, gas (pressure) is delivered along path C from the air pump 215, through the branched line in the connector portion 265 and out of the gas supply tubing 240*c* to the water reservoir 305. The gas (pressure) pressurizes the surface of the remaining water 285 in the reservoir 305 and pushes water up the lens wash supply tube 245*c* to the connector portion 265. The pressurized lens wash water is pushed further through the lens wash feed line 245*b* in the umbilical 260 and through the gas/water valve 140. Since the system 300 is closed, gas pressure is allowed to build and maintain a calibrated pressure level in the water reservoir 305, rather than venting to atmosphere or being delivered to the patient. This pressure, along with the endoscope feed and supply lines and external tubing, translates to a certain range of flow rate of the lens wash.

Figure 3D:
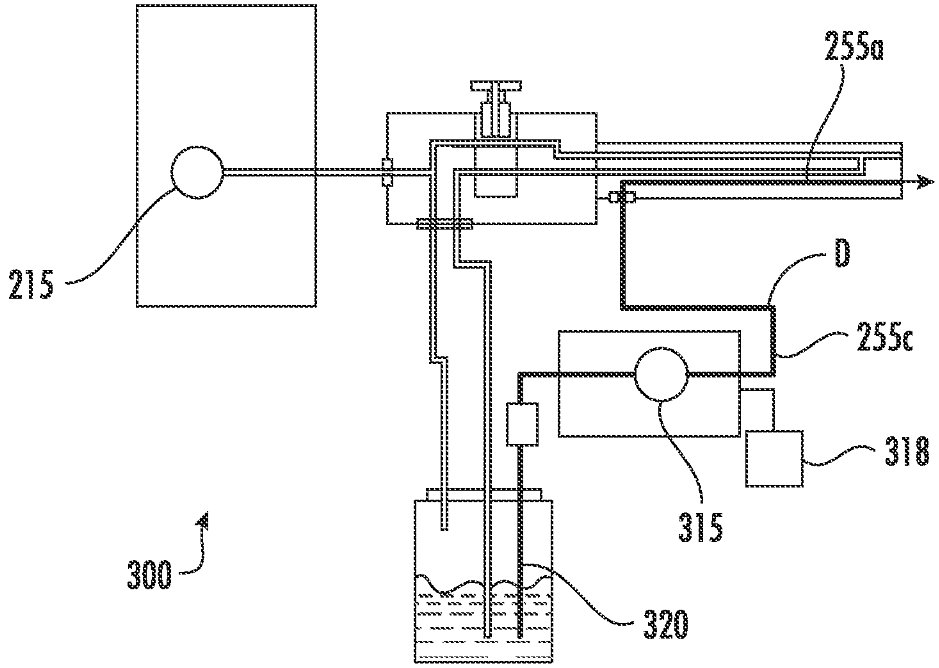
FIG. 3D depicts the endoscope system of FIG. 3A, wherein the system is activated to deliver irrigation fluid through the patient end of the endoscope.

As shown in FIG. 3D, the endoscope 100 is in an irrigation delivery state. This may be performed at the same or a different time from the delivery of gas and/or lens wash. When irrigation is called for at the distal tip 100*c*, for example, if visibility in the treatment area is poor or blocked by debris, or the like, the user activates the irrigation pump 315 (e.g., by depressing foot switch 318) to deliver water along path D. With the pump 315 activated, water is sucked out of the water reservoir 305 through the upstream irrigation supply tubing 320 and pumped along the downstream irrigation supply tubing 255*c* to the connector portion 265. The irrigation pump head pressure pushes the irrigation water further through the irrigation feed line 255*b* in the umbilical 260, through the irrigation supply line 255*a* in the endoscope shaft 100*a*, and out the irrigation opening 225 at the distal tip 100*c*. The irrigation pump pressure may be calibrated, along with the endoscope irrigation feed and supply lines and external tubing, to deliver a certain range of flow rate of the irrigation fluid.

Figure 4:
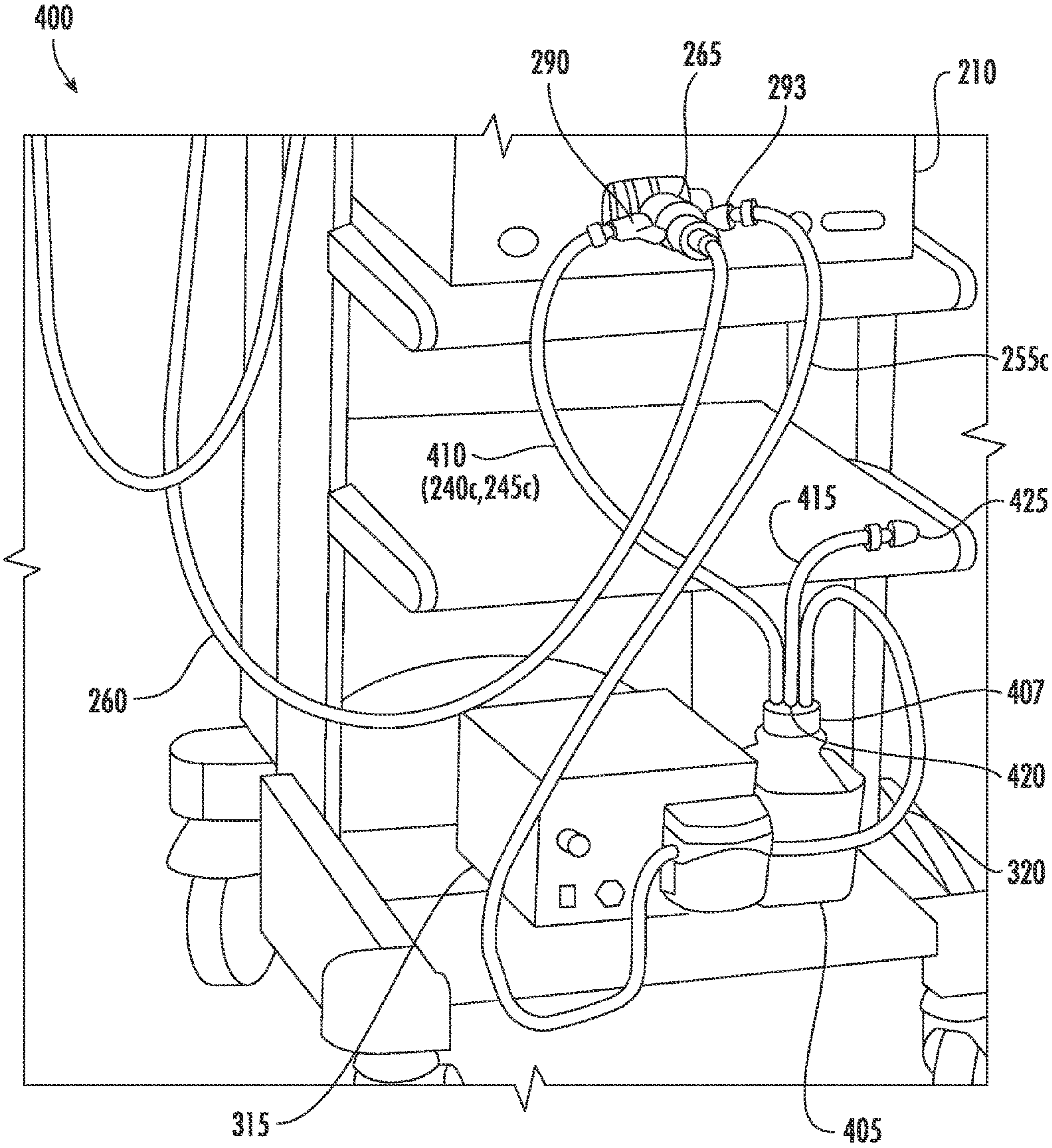
FIG. 4 depicts a hybrid endoscope system including a video processing unit, connector portion, peristaltic irrigation pump, water reservoir and top, coaxial gas and lens wash supply tubing, upstream and downstream irrigation supply tubing, and alternative gas supply tubing.

FIG. 4 is a schematic drawing illustrating a further embodiment of a hybrid system 400 including a video processing unit 210, connector portion 265, peristaltic irrigation pump 315, water reservoir 405 and top 407, coaxial gas and lens wash supply tubing 410, upstream and downstream irrigation supply tubing 320, 255*c*, respectively, and alternative gas (e.g., $CO_2$) supply tubing 415. A length of the alternative gas supply tubing 415 passes from one end positioned in the gas gap 275 (see FIG. 2) between the top 407 of the water reservoir 405 and the remaining water 285 in the reservoir through an additional opening 420 in the top of the reservoir to a detachable connection 425 for a source of the alternative gas supply (e.g., $CO_2$ hospital house gas source). When the alternative gas supply is desired, such as $CO_2$ gas, the air pump 215 on the video processing unit 210 may be turned off and $CO_2$ gas, rather than air, is thereby flowed to the water reservoir 405 pressurizing the water surface. Generally, the flow of $CO_2$ through the endoscope 100 is similar to the flow of air. In the neutral state, $CO_2$ gas flows backward up the gas supply tubing 240*c* to the connector portion 265, up the gas feed line 240*b*, and is vented through the gas/water valve 140 to atmosphere. In the first position, the user closes off the vent hole in the gas/water valve 140, and the $CO_2$ gas is flowed through the gas/water valve to the gas supply line 240*a* in the endoscope shaft 100*a* and out the gas/lens wash nozzle 220 at the distal tip 100*c*. In the second position, the user depresses the valve 140 to the bottom of the valve well 135, keeping the vent hole in the gas/water valve closed off. The second position blocks the $CO_2$ gas supply to both atmosphere and the gas supply line 240*a* in the endoscope 100, and opens up the gas/water valve 140 to allow lens wash water to pass through to the lens wash supply line 245*a* in the endoscope shaft 100*a* and out the gas/lens wash nozzle 220 at the distal tip 100*c*. Gas (pressure) in the reservoir 405 is maintained by delivering gas through alternative gas (e.g., $CO_2$) supply tubing 415. The irrigation function may be accomplished in a similar manner as the operation described above with respect to FIG. 3D.

Figure 5:
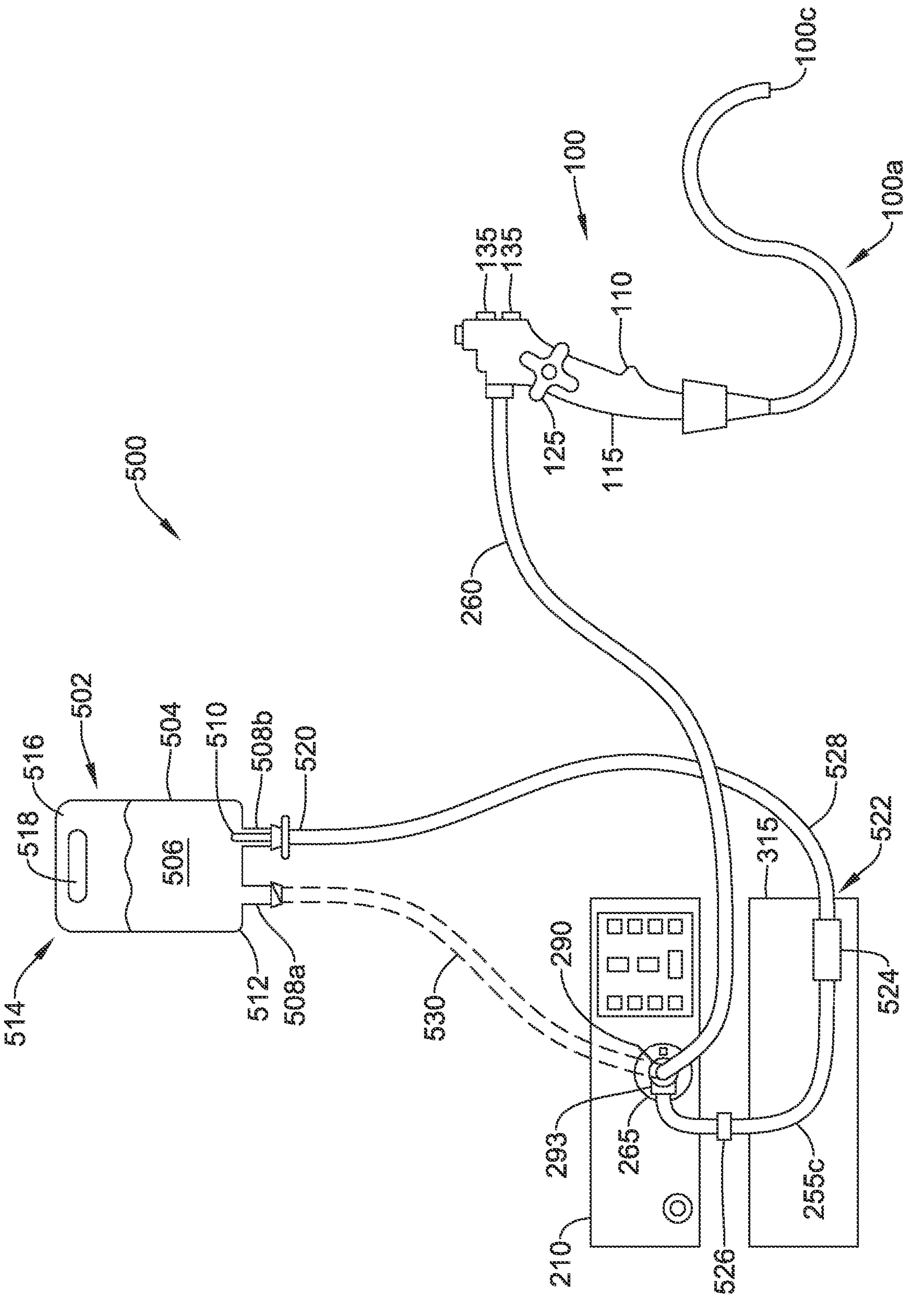
FIG. 5 depicts another illustrative endoscope system having an alternative irrigation fluid supply container.

As described above, it may be desirable to reduce opportunities for contamination to the tube set 240*c*, 245*c*, 320, 410, 415 during replacement of the water reservoir(s). FIG. 5 depicts a schematic view of an illustrative endoscopic system 500 which may reduce the number of water reservoir changes and/or reduce opportunities for contamination during replacement of the water reservoir(s). The system 500 may include components similar to the endoscope and endoscope systems described with regard to FIGS. 1-4; however, not all features may be described or shown here.

The system 500 of FIG. 5 depicts an illustrative fluid reservoir 502 that may include a number of advantages over the current bottle system described above. The reservoir 502 may include a container 504 configured to hold a fluid 506. In the illustrated embodiment, the container 504 is fluidly coupled to the upstream irrigation tubing 528 and is configured to provide fluid for irrigation to the endoscope 100. Generally, the irrigation tubing 528 may be a water or fluid supply line or tube for supplying water or other fluid to an endoscope 100. Alternatively, or additionally, the container 504 may be coupled to a gas and lens wash supply tubing 530 to provide insufflation and fluid for clearing the lens. Further, in some cases, the reservoir 502 may supply fluid for both irrigation and lens wash. While not explicitly shown, the reservoir 502 may include printed lines, numbers, or other visual indicia to allow a user to easily determine how much fluid is left in the reservoir 502.

The container 504 may be formed from one or more layers of a lightweight, flexible material, such as, but not limited to, low density polyethylene (LDPE), thermoplastic polyurethane (TPU), silicone, polyethylene terephthalate (PET), aluminum, nylon, polyethylene (PE), plasticized polyvinyl chloride (PVC), or combinations thereof, etc. In some embodiments, the container 504 may be entirely translucent, entirely opaque, or combinations thereof. In some cases, the container 504 may be a flexible bag analogous to those utilized to deliver intravenous replacement fluid in clinical settings (for example, an intravenous (IV) fluid bag). Such bags may be readily available and familiar to the clinician as they are widely used in various sizes. The volume of the container 504 may be variable. For example, the volume of the container 504 may be 500 milliliters (mL) or greater, 1000 mL or greater, 2000 mL or greater, 3000 mL, 4000 mL or greater, etc. The volume may be less than 500 mL or greater than 4000 mL, as desired. The reservoir 502 may be pre-filled (e.g., prior to entering the procedure suite or at the time of manufacturing) with water or other fluid. In some cases, the clinician may select the reservoir 502 from a plurality of differently sized available reservoirs based on the number and/or types of procedures expected for a day. By selecting a reservoir 502 having a volume large enough to accommodate an entire day of procedures, the need for replacing the sterile fluid source (e.g., the reservoir 502) may be reduced or eliminated. It is contemplated that flexible bags may utilize less plastic (or other material) than a bottle designed to hold a similar amount of fluid. Thus, the use of a flexible bag as a fluid reservoir 502 may increase the level of environmental sustainability of the system 500. For example, if the user sets up the system with a 3000 mL (3 liter) bag reservoir 502 and therefore does not need to utilize three individual one liter bottles, a significant reduction of waste may be realized. It is further contemplated that when disposed of or discarded, a bag reservoir 502 may occupy less volume than a bottle capable of holding an equivalent amount of fluid.

The reservoir 502 may further include one or more ports 508*a*, 508*b*, such as, but not limited to a spike port or a septum port, extending from and in selective fluid communication with an interior of the container 504. The ports 508*a*, 508*b* may be formed as a monolithic structure with the first container 504. The ports 508*a*, 508*b* may be generally tubular structures with each port 508*a*, 508*b* defining a lumen extending therethrough. The lumens of the ports 508*a*, 508*b* may be configured to selectively fluidly couple the interior of the container 504 with another component, such as, but not limited to, a water or fluid supply tube. In some embodiments, the ports 508*a*, 508*b* may be positioned adjacent to a bottom end 512 of the reservoir 502. However, this is not required. The ports 508*a*, 508*b* may be positioned in other locations, as desired. If the ports 508*a*, 508*b* are positioned at a location other than the bottom end 512 of the container 504, a dip tube or tube extension may be required to access the fluid at the bottom of the container 504. In some cases, at least one port 508*b* may be configured to be coupled to the upstream irrigation tubing (or water/fluid supply tube) 528 while the other port 508*a* may be configured to allow the user to add additives to the fluid 506 (e.g., irrigation fluid). While the reservoir 502 is illustrated as including two ports 508*a*, 508*b*, the reservoir 502 may include one port or more than two ports, as desired.

While not explicitly shown, the ports 508*a*, 508*b* may each include a removable cap or seal configured to form a fluid tight seal with the port 508*a*, 508*b*. The removable cap or seal may help to maintain the sterility of the ports 508*a*, 508*b*. The removable cap or seal may be coupled to a free end of the ports 508*a*, 508*b* using a number of different techniques. For example, the cap or seal may be coupled to the port 508*a*, 508*b* using a threaded engagement, a friction fit, a snap fit, etc. In other instances, the cap or seal may be removed through a twisting motion configured to break the cap or seal from the port 508*a*, 508*b*. Once the cap or seal has been removed, the port 508*a*, 508*b* may be pierced with a spike tip or spike port adaptor 510 that is coupled to the upstream irrigation tubing 528. For example, in addition to the removable cap or seal, the port 508*a*, 508*b* may include an internal seal disposed within a lumen of the port 508*a*, 508*b* that may be punctured or pierced by the spike port adaptor 510. The internal seal may be configured to prevent fluid 506 from leaking from the container 504 prior to the spike port adaptor 510 being inserted into the port 508*a*, 508*b*. In some embodiments, the internal seal may be self-sealing such that upon removal of the spike port adaptor 510 fluid is prevented from leaking from the port 508*a*, 508*b*. The outer surface of the spike port adaptor 510 may form an interference fit with the inner surface of the port 508*a*, 508*b*. The fit and/or coupling between the spike port adaptor 510 and the port 508*a*, 508*b* may be sufficient to remain in place when the irrigation supply tube 528 and/or other tubing sets are coupled to the spike port adaptor 510. It is contemplated that the spike port adaptor 510 may be inserted into one of the ports 508*a*, 508*b* utilizing universally used aseptic techniques such as those used with IV fluid bags. This may help reduce infection risk by maintaining sterile components, not introducing contaminants into the fluid 506, etc. It is further contemplated that additives may be added to the fluid 506 using similar aseptic techniques via one of the ports 508*a*, 508*b*.

The reservoir 502 may include a handle 516 positioned adjacent to a top portion 514 thereof. The handle 516 may define an opening or through hole 518 for receiving a hand or hook therethrough to carry the reservoir 502. In some cases, the handle 516 may include an undulating surface configured to provide a more ergonomic grip for the user. It is contemplated that the handle 516 may be formed from a similar material as the container 504 or a different material, as desired. In some examples, the handle 516 may be formed from polyethylene terephthalate (PET), polypropylene (PP), etc. The handle 516 may allow the reservoir 502 to be hung from a hook, such as, but not limited to an IV stand. Hanging the reservoir 502 may allow the reservoir 502 to be positioned above the level of an endoscope cart which may enable the user to see the fluid 506 level at any time. This may help the clinician avoid running out of fluid during a procedure. Additionally, elevating the reservoir may eliminate the need for the clinician to bend or stoop during setup of the system 500 and/or to change the reservoir 502. In some cases, head pressure generated from elevating the reservoir 502 may enable rapid priming of the irrigation circuit (and/or lens wash circuit if so connected) which may save time during setup. It is further contemplated that hanging the reservoir 502 from a hook or IV stand may allow the reservoir 502 to be positioned away from expensive capital equipment thus reducing or eliminating the potential for fluid running or flowing inadvertently onto the capital equipment and causing damage or destruction.

The reservoir 502 may be connected in fluid communication with a lumen of an upstream irrigation supply tube 528. The upstream irrigation supply tube 528 extends from a second end region 522 external to the container 504 and positioned within a pump head 524 of the peristaltic irrigation pump 315 to a first end 520. The first end 520 is coupled to the spike port adaptor 510 which in turn is configured to extend through a lumen of the port 508*b* and pierce a seal within the lumen of the port 508*b* to fluidly couple the interior of the container 504 with the lumen of the upstream irrigation supply tube 528. The second end of the upstream irrigation supply tube 528 is configured to be fluidly coupled with an irrigation lumen of the endoscope 100. When irrigation water is required, fluid is pumped from the container 504 by operating the irrigation pump 315, such as by depressing a footswitch (not shown), and flows from the reservoir 502, through the upstream irrigation supply tubing 528, through the downstream irrigation supply tubing 255*c*, through the irrigation connection 293, through the irrigation feed line 255*b* in the umbilical 260, and down the irrigation supply line 255*a* in the shaft 100*a* of the endoscope to the distal tip 100*c*.

The downstream irrigation supply tubing 255*c* may include a loaded check valve or flow control valve 526 positioned in line with the downstream irrigation supply tubing 255*c*. The flow control valve 526 may prevent the unintentional flow of fluid from the container 504 to the endoscope 100. In some cases, the flow control valve 526 may be configured to open when the pressure within the downstream irrigation supply line 255*c* reaches a predetermined minimum pressure. It is contemplated that the predetermined minimum pressure may be greater than the head pressure created by the height differential between the reservoir 502 and the irrigation pump 315. The flow control valve 526 may also prevent fluid from leaking from the downstream irrigation supply tube 255*c* when the endoscope 100 is changed between patients.

In some embodiments, the irrigation pump 315 may be omitted. For example, the reservoir 502 may be inserted into a compression sleeve. When irrigation fluid is desired, the compression sleeve may be activated to exert pressure on an outer surface of the reservoir 502 and to provide the required pressure to perform irrigation at the distal end of the endoscope 100.

In some embodiments, a lens wash supply tubing 530 may be coupled to the first port 508*a*. In this embodiment, the lens wash supply tubing and the irrigation supply tubing 528 may be coupled to the same reservoir 502. The reservoir 502 may be inserted into a compression sleeve, as described above. The pressure exerted by the compression sleeve may be sufficient to supply pressurized fluid for both irrigation and lens wash to the endoscope without the use of a secondary pump (such as an irrigation pump) or pressure source (such as an insufflator).

If there is a need to replace the reservoir 502 with a new full bag, for example when the reservoir 502 is empty or near empty, the user may, optionally, hang the new bag near the reservoir 502 to be replaced. The user may then disengage the spike port adaptor 510 from the port 508*b* and insert the spike port adaptor 510 into a port of the new bag. This may be performed without requiring the clinician to bend or stoop to access the reservoir 502. The port 508*b* may self-seal to prevent fluid leaks from the reservoir 502 as it is being replaced or upon removal of the spike port adaptor 510. This method of replacing the reservoir 502 may have a lower risk of introducing contaminants into the systems relative to traditional bottle systems. For example, the change out method described herein may allow the reservoir 502 to be changed out without having tubing dangling from a cap (as in a bottle system). Further, the system 500 may remain largely closed as the reservoir 502 is changed out.

Figure 6:
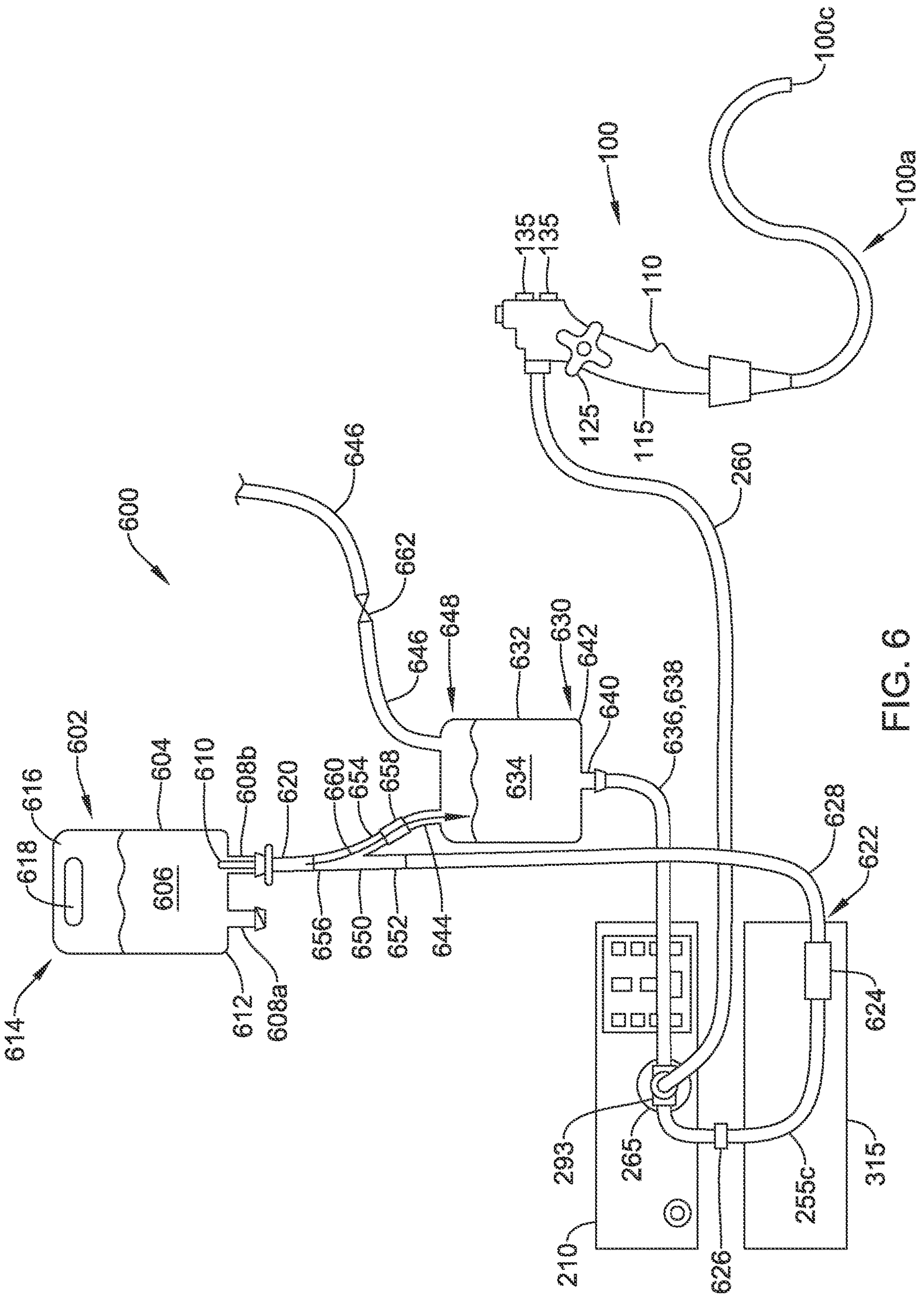
FIG. 6 depicts another illustrative endoscope system having an alternative fluid supply system.

FIG. 6 depicts a schematic view of another illustrative endoscopic system 600 which may reduce the number of water reservoir changes and/or reduce opportunities for contamination during replacement of the water reservoir(s). The system 600 may include a number of advantages over the current bottle system described above. The system 600 may include components similar to the endoscope and endoscope systems described with regard to FIGS. 1-4; however, not all features may be described or shown here.

Generally, the system 600 may include a first reservoir 602 and a second reservoir 630. The first reservoir 602 may be configured to supply water or fluid for both irrigation (e.g., via the first reservoir 602) and lens wash (e.g., via the second reservoir 630). This may allow a single fluid source to be used to provide fluid for both irrigation and lens wash. While not explicitly shown, the reservoirs 602, 630 may include printed lines, numbers, or other visual indicia to allow a user to easily determine how much fluid is left in the reservoirs 602, 630.

The first reservoir 602 may include a first container 604 configured to hold a first volume of fluid 606. In the illustrated embodiment, the first container 604 is fluidly coupled to the upstream irrigation supply tubing 628 and is configured to provide fluid for irrigation to the endoscope 100. Generally, the irrigation supply tubing 628 may be a water or fluid supply line or tube for supplying water or other fluid to an endoscope. Additionally, the first container 604 may be selectively fluidly coupled to a second fluid reservoir 630. The second reservoir 630 may include a second container 632 configured to hold a second volume of fluid 634. In the illustrated embodiment, the second container 632 is fluidly coupled to the gas and lens wash supply tubing 636, 638 and is configured to provide fluid for lens wash to the endoscope 100. Generally, the lens wash supply tubing 638 may be a water or fluid supply line or tube for supplying water or other fluid to an endoscope. The gas and lens wash supply tubing 636, 638 may be coaxially arranged. For example, the gas supply tubing 636 may define a lumen that is sufficiently large in diameter to encompass a smaller diameter lens wash tubing 638, coaxially received within the gas supply tubing, as well as provide air to the water source in an annular space surrounding the lens wash tubing 638 to pressurize the second reservoir 630. The lens wash supply tubing 638 may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion 265. In other embodiments, the gas and lens wash supply tubing 636, 638 may be arranged in a side-by-side arrangement.

The first and second containers 604, 632 may be formed from one or more layers of a lightweight, flexible material, such as, but not limited to, low density polyethylene (LDPE), thermoplastic polyurethane (TPU), silicone, polyethylene terephthalate (PET), aluminum, nylon, polyethylene (PE), plasticized polyvinyl chloride (PVC), or combinations thereof, etc. In some embodiments, the first and second containers 604, 632 may be entirely translucent, entirely opaque, or combinations thereof. In some cases, the first and second containers 604, 632 may be a flexible bag analogous to those utilized to deliver intravenous replacement fluid in clinical settings (for example, an intravenous (IV) fluid bag). Such bags may be readily available and familiar to the clinician as they are widely used in various sizes. The volume of the first and second containers 604, 632 may be variable. For example, the volume of the first container 604 and/or the second container 632 may be 500 milliliters (mL) or greater, 1000 mL or greater, 2000 mL or greater, 3000 mL, 4000 mL or greater, etc. The volume may be less than 500 mL or greater than 4000 mL, as desired. One or both of the first and second reservoirs 602, 630 may be pre-filled (e.g., prior to entering the procedure suite or at the time of manufacturing) with water or other fluid. In some cases, the clinician may select the reservoir(s) 602, 630 from a plurality of differently sized available reservoirs based on the number and/or types of procedures expected for a typical or the specific day. In the illustrated embodiments, the first reservoir 602 may supply fluid to the second reservoir 630. By selecting a first reservoir 602 having a volume large enough to accommodate an entire day of procedures, the need for replacing the sterile fluid source (e.g., the first reservoir 602) may be reduced or eliminated. In some cases, the first reservoir 602 may be used to periodically refill the second reservoir 630. Thus, the volume of the first reservoir 602 may be greater than the volume of the second reservoir 630, although this is not required. It is further contemplated that, in some embodiments, one or both of the first or second reservoirs 602, 630 may be a rigid bottle.

It is contemplated that flexible bags may utilize less plastic (or other material) than a bottle designed to hold a similar amount of fluid. Thus, the use of a flexible bag as a fluid reservoir 602, 630 may increase the level of environmental sustainability of the system 600. For example, if the user sets up the system with a 3000 mL (3 liter) bag reservoir 602 and therefore does not need to utilize three individual one liter bottles, a significant reduction of waste may be realized. It is further contemplated that when disposed of or discarded, a flexible bag reservoir may occupy less volume than a bottle capable of holding an equivalent amount of fluid.

The first reservoir 602 may further include one or more ports **608*a*, 608*b*, such as, but not limited to a spike port or a septum port, extending from and in selective fluid communication with an interior of the first container 604. The ports 608*a*, 608*b* may be formed as a monolithic structure with the first container 604. The ports 608*a*, 608*b* may be generally tubular structures with each port 608*a*, 608*b* defining a lumen extending therethrough. The lumens of the ports 608*a*, 608*b* may be configured to selectively fluidly couple the interior of the first container 604 with another component, such as, but not limited to, a fluid or water supply tube. In some embodiments, the ports 608*a*, 608*b* may be positioned adjacent to a bottom end 612 of the first reservoir 602. However, this is not required. The ports 608*a*, 608*b* may be positioned in other locations, as desired. If the ports 608*a*, 608*b* are positioned at a location other than the bottom end 612 of the first container 604, a dip tube or tube extension may be required to access the fluid at the bottom of the first container 604. In some cases, at least one port 608*b* may be configured to be coupled to the upstream irrigation tubing (or water supply tube) 628 while another port 608*a* may be configured to allow the user to add additives to the fluid 606. While the first reservoir 602 is illustrated as including two ports 608*a*, 608*b*, the first reservoir 602** may include one port or more than two ports, as desired.

While not explicitly shown, the ports **608*a*, 608*b* may each include a removable cap or seal configured to form a fluid tight seal with the port 608*a*, 608*b*. The removable cap or seal may help to maintain the sterility of the ports 608*a*, 608*b*. The removable cap or seal may be coupled to a free end of the ports 608*a*, 608*b* using a number of different techniques. For example, the cap or seal may be coupled to the port 608*a*, 608*b* using a threaded engagement, a friction fit, a snap fit, etc. In other instances, the cap or seal may be removed through a twisting motion configured to break the cap or seal from the port 608*a*, 608*b*. Once the cap or seal has been removed, the port 608*a*, 608*b* may be pierced with a spike tip or spike port adaptor 610 that is coupled to the upstream irrigation tubing 628. For example, in addition to the removable cap or seal, the port 608*a*, 608*b* may include an internal seal disposed within a lumen of the port 608*a*, 608*b* that may be punctured or pierced by the spike port adaptor 610. The internal seal may be configured to prevent fluid 606 from leaking from the first container 604 prior to the spike port adaptor 610 being inserted into the port 608*a*, 608*b*. In some embodiments, the internal seal may be self-sealing such that upon removal of the spike port adaptor 610 fluid is prevented from leaking from the port 608*a*, 608*b*. The outer surface of the spike port adaptor 610 may form an interference fit with the inner surface of the port 608*a*, 608*b*. The fit and/or coupling between the spike port adaptor 610 and the port 608*a*, 608*b* may be sufficient to remain in place when the irrigation supply tube 628, branched connector 650, and/or other tubing sets are coupled to the spike port adaptor 610. It is contemplated that the spike port adaptor 610 may be inserted into one of the ports 608*a*, 608*b* utilizing universally used aseptic techniques such as those used with IV fluid bags. This may help reduce infection risk by maintaining sterile components, not introducing contaminants into the fluid 606, etc. It is further contemplated that additives may be added to the fluid 606 using similar aseptic techniques via one of the ports 608***a*, 608*b*.

The first reservoir 602 may include a handle 616 positioned adjacent to a top portion 614 thereof. The handle 616 may define an opening or through hole 618 for receiving a hand or hook therethrough to carry the first reservoir 602. In some cases, the handle 616 may include an undulating surface configured to provide a more ergonomic grip for the user. It is contemplated that the handle 616 may be formed from a similar material as the first container 604 or a different material, as desired. In some examples, the handle 616 may be formed from polyethylene terephthalate (PET), polypropylene (PP), etc. The handle 616 may allow the first reservoir 602 to be hung from a hook, such as, but not limited to an IV stand. Hanging the first reservoir 602 may allow the first reservoir 602 to be positioned above the level of an endoscope cart which may enable the user to see the fluid 606 level at any time. This may help the clinician avoid running out of fluid during a procedure. Additionally, elevating the reservoir may eliminate the need for the clinician to bend or stoop during setup of the system 600 and/or to change the first reservoir 602. In some cases, head pressure generated from elevating the first reservoir 602 may enable rapid priming of the irrigation circuit (and/or lens wash circuit if so connected) which may save time during setup. It is further contemplated that hanging the first reservoir 602 from a hook or IV stand may allow the first reservoir 602 to be positioned away from expensive capital equipment thus reducing or eliminating the potential for fluid running or flowing inadvertently onto the capital equipment and causing damage or destruction.

The first reservoir 602 may be connected in fluid communication with a lumen of the upstream irrigation supply tube 628. The upstream irrigation supply tube 628 extends from a second end region 622 external to the container 604 and positioned within a pump head 624 of the peristaltic irrigation pump 315 to a first end 620. The first end 620 of the upstream irrigation supply tube 628 is coupled to the spike port adaptor 610 which in turn is configured to extend through a lumen of the port 608*b* and pierce a seal within the lumen of the port 608*b* to fluidly couple the interior of the container 604 with the lumen of the upstream irrigation supply tube 628. The second end of the upstream irrigation supply tube 628 is configured to be fluidly coupled with an irrigation lumen of the endoscope 100. When irrigation water is required, fluid is pumped from the first container 604 by operating the irrigation pump 315, such as by depressing a footswitch (not shown), and flows from the first reservoir 602, through the upstream irrigation supply tubing 628 and a branched connector 650, through the downstream irrigation supply tubing 255*c*, through the irrigation connection 293, through the irrigation feed line 255*b* in the umbilical 260, and down the irrigation supply line 255*a* in the shaft 100*a* of the endoscope to the distal tip 100*c*.

The downstream irrigation supply tubing 255*c* may include a loaded check valve or flow control valve 626 positioned in line with the downstream irrigation supply tubing 255*c*. The flow control valve 626 may prevent the unintentional flow of fluid from the first container 604 to the endoscope 100. In some cases, the flow control valve 626 may be configured to open when the pressure within the downstream irrigation supply line 255*c* reaches a predetermined minimum pressure. It is contemplated that the predetermined minimum pressure may be greater than the head pressure created by the height differential between the first reservoir 602 and the irrigation pump 315. The flow control valve 626 may also prevent fluid from leaking from the downstream irrigation supply tube 255*c* when the endoscope 100 is changed between patients and the tubing set connector is separated from the endoscope water port.

In some embodiments, the irrigation pump 315 may be omitted. For example, the reservoir 602 may be inserted into a compression sleeve. When irrigation fluid is desired, the compression sleeve may be activated to exert pressure on an outer surface of the reservoir 602 and to provide the required pressure to perform irrigation at the distal end of the endoscope 100. In another embodiment the reservoir 602 may be inserted into a compression sleeve which applies constant pressure to the reservoir 602 with a flow switch positioned along irrigation supply tubing 628 to provide binary control of irrigation flow.

The second reservoir 630 may further include one or more ports 640, such as, but not limited to a spike port or a septum port, extending from and in selective fluid communication with an interior of the second container 632. The port 640 may be formed as a monolithic structure with the second container 632. The port 640 may be a generally tubular structure with the port 640 defining a lumen extending therethrough. The lumen of the port 640 may be configured to selectively fluidly couple the interior of the second container 632 with another component, such as, but not limited to, fluid/water/gas supply tube(s). In some cases, the port 640 may be configured to be coupled to the gas and lens wash supply tubing 636, 638. In some embodiments, the port 640 may be positioned adjacent to a bottom end 642 of the second reservoir 630. However, this is not required. The port 640 may be positioned in other locations, as desired. If the port 640 is positioned at a location other than the bottom end 642 of the second container 632, a dip tube or tube extension may be required (e.g., coupled to the lens wash supply tubing 638) to access the fluid at the bottom of the second container 632. While the second reservoir 630 is illustrated as including one port 640, the second reservoir 630 may include more than one port, as desired.

While not explicitly shown, the port 640 may include a removable cap or seal configured to form a fluid tight seal with the port 640. The removable cap or seal may help to maintain the sterility of the port 640. The removable cap or seal may be coupled to a free end of the port 640 using a number of different techniques. For example, the cap or seal may be coupled to the port 640 using a threaded engagement, a friction fit, a snap fit, etc., or may be fixedly coupled using a number of techniques such as adhesive or solvent bonding. In other instances, the cap or seal may be removed through a twisting motion configured to break the cap or seal from the port 640. Once the cap or seal has been removed, the port 640 may be pierced with a spike tip or spike port adaptor (not explicitly shown) that is coupled to the gas and lens wash supply tubing 636, 638. For example, in addition to the removable cap or seal, the port 640 may include an internal seal disposed within a lumen of the port 640 that may be punctured or pierced by the spike port adaptor. The internal seal may be configured to prevent fluid 634 from leaking from the second container 632 prior to the spike port adaptor being inserted into the port 640. In some embodiments, the internal seal may be self-sealing such that upon removal of the spike port adaptor fluid is prevented from leaking from the port 640. The outer surface of the spike port adaptor may form an interference fit with the inner surface of the port 640. The fit and/or coupling between the spike port adaptor and the port 640 may be sufficient to remain in place when the gas and fluid supply tubing 636, 638 and/or other tubing sets are coupled to the spike port adaptor 610. It is contemplated that the spike port adaptor may be inserted into one of the ports 640 utilizing universally used aseptic techniques such as those used with IV fluid bags. This may help reduce infection risk by maintaining sterile components, not introducing contaminants into the fluid 634, etc. It is further contemplated that additives may be added to the fluid 634 using similar aseptic techniques via the port 640, if so desired. In some cases, other coupling mechanisms may be used as desired to couple the gas and lens wash supply tubing 636, 638 to the port 640. Some illustrative coupling mechanisms may include, but are not limited to, threaded engagements, snap fits, friction fits, quick connect style couplers, etc., or may be fixedly coupled using a number of techniques such as adhesive or solvent bonding.

The gas supply tubing 636 extends from a second end external to the second container 632 to the port 640. The gas supply tubing 636 may extend into the interior of the second container 632 and terminate within a reservoir gap (e.g., above the level of the fluid 634). However, in some cases, the gas supply tubing 636 may terminate within the fluid 634. A lumen extends through the gas supply tubing 636 for receiving a flow of air and/or gas therethrough. The lumen of the gas supply tubing 636 may be in operative fluid communication with a top portion of the interior of the second container 632. The lens wash supply tubing 638 extends from a second end external to the second reservoir 630 to a first end in fluid communication with a bottom portion 642 of the second container 632. In some embodiments, the lens wash supply tubing 638 may terminate at the port 640. A lumen extends through the lens wash supply tubing 638 for receiving a flow of fluid therethrough. The lumen of the lens wash supply 638 is in selective operative fluid communication with a bottom portion 642 of the second container 632. In the illustrated embodiment, the gas supply tubing 636 and the lens wash supply tubing 638 may couple to the second container 632 through a single or common opening (e.g., port 640). For example, the gas supply tubing 636 and the lens wash supply tubing 638 may be coaxially arranged. However, this is not required. In some cases, the gas supply tubing 636 and the lens wash supply tubing 638 may extend in a side by side arrangement or may be separately connected to the second container 632 in different locations.

The second container 632 may further include a first fluid inlet 644 and a second fluid inlet 646. While the first and second fluid inlets 644, 646 are illustrated as being adjacent to or extending from a top portion 648 of the second container 632, the first and/or second fluid inlets 644, 646 may be positioned at other locations about the second container 632, as desired. In some embodiments, the first and/or second fluid inlets 644, 646 may be tubular members formed as a single monolithic structure with the second container 632. In other embodiments, the first and/or second fluid inlets 644, 646 may include tubular components releasably coupled to ports (similar in form and function to port 640) formed in or with the container 632.

The first fluid inlet 644 may be in selective fluid communication with the first reservoir 602. For example, a branched connector 650 may be positioned in-line with the upstream irrigation tubing 628. In some embodiments, the branched connector 650 may be a “Y” connector or a “T” connector having an inlet leg 656 defining a first fluid inlet, a first outlet leg 652 defining a first fluid outlet, and a second outlet leg 654 defining a second fluid outlet. However, it is contemplated that the branched connector 650 may include more than one fluid inlet and fewer than two or more than two fluid outlets, if so desired.

The branched connector 650 may be positioned in-line with the upstream irrigation tubing 628 such that the inlet leg 656 and the first outlet leg 652 are fluidly coupled with the lumen of the upstream irrigation tubing 628. Fluid may flow from the first reservoir 602, through the upstream irrigation tubing 628, through the branched connector 650 and again through the upstream irrigation tubing 628. The branched connector 650 may be positioned such that the inlet leg 656 is upstream of the outlet legs 652, 654 relative to a flow of irrigation fluid. In some embodiments, the branched connector 650 and the spike port 610 may be molded or formed as a single monolithic structure. It is contemplated that this may reduce connection points in the fluid circuit. In such an instance, the first end 620 of the irrigation supply tubing 628 may be fluidly coupled to the first outlet leg 652 of the branched connector 650.

The second outlet leg 654 may be fluidly coupled to the first fluid inlet 644 of the second reservoir 630. A flow control mechanism, such as, but not limited to, a one-way valve 658 may be positioned between the second fluid outlet of the second outlet leg 654 and the first fluid inlet 644 of the second reservoir 630 to selectively fluidly couple the second container 632 with the first container 604. The one-way valve 658 may be configured to be opened to allow fluid to selectively pass from the first reservoir 602 to the second reservoir 630 while preventing fluid (e.g., gas, water, or other fluid) from exiting the second container 632 and entering the irrigation supply tubing 628 and/or the first container 604. In some embodiments, the one-way valve 658 may be replaced with a clamp which may compress the first fluid inlet 644 to selectively fluidly isolate the second container 632 from the first container 604 and removed to selectively couple the second container 632 with the first container 604. In yet other embodiments, the one-way valve 658 may be replaced with a spring-loaded valve, a stopcock, or other two-way valve. When it is desired to add fluid to the second reservoir 630 from the first reservoir 602, the one-way valve 658 (or other flow control mechanism) may be opened or released. Fluid may then be at least partially diverted from the irrigation supply tubing 628 through the second outlet leg 654 of the branched connector 650 and into the second container 632 along flow path 660. Fluid may be added to the second container 632 while the irrigation pump 315 is running or while the irrigation pump 315 is idle, as desired.

In an alternative embodiment, the branched connector 650 may be positioned within an interior of the second container 632. For example, the inlet leg 656 may be fluidly coupled to the first fluid inlet 644 within an interior of the second container 632. The branched connector 650 may be positioned in-line with the upstream irrigation tubing 628 such that the inlet leg 656 and the first outlet leg 652 are fluidly coupled with the lumen of the upstream irrigation tubing 628. The upstream irrigation tubing 628 may extend through the interior of the second container 632 and exit via a second fluid outlet (not explicitly shown). In some embodiments, the second fluid outlet may be a tubular member formed as a single monolithic structure with the second container 632. In other embodiments, the second fluid outlet may include a tubular component releasably coupled to a port (similar in form and function to port 640) formed in or with the container 632. The fluid within the upstream irrigation tubing 628 may remain fluidly isolated from the fluid 634 within the second container 632. Fluid may flow from the first reservoir 602, through the upstream irrigation tubing 628, through the branched connector 650 and again through the upstream irrigation tubing 628. The second outlet leg 654 may be positioned within the interior of the second container 632 such that fluid selectively flows through the second outlet leg 654 into the interior of the second container 632.

The second fluid inlet (or gas supply tube) 646 of the second container 632 may be an alternative gas supply tubing configured to be coupled to an alternative gas supply (e.g., $CO_2$ hospital house gas source). The second fluid inlet 646 may extend from a second end external to the second container 632 to a first end coupled to the second container 632. The alternative gas supply may be used to pressurize the second container 632 to supply lens wash to the endoscope 100 and/or to provide insufflation. A lumen extends through the second fluid inlet 646 for receiving a flow of gas therethrough. The lumen of the second fluid inlet 646 is in operative fluid communication with a top portion of the second container 632. The flow of the $CO_2$ through the system 600 may be similar to that described above. For example, in the neutral state, $CO_2$ gas flows through the second fluid inlet 646 into the second container 632, up the gas supply tubing 636 to the connector portion 265, up the gas feed line 240*b* in the umbilical 260, and is vented through the gas/water valve 140 to atmosphere. In the first position, the user closes off the vent hole in the gas/water valve 140, and the $CO_2$ gas is flowed through the second fluid inlet 646 into the second container 632, up the gas supply tubing 636 to the connector portion 265, through the gas/water valve to the gas supply line 240*a* in the endoscope shaft 100*a* and out the gas/lens wash nozzle 220 at the distal tip 100*c*. In the second position, the user depresses the valve 140 to the bottom of the valve well 135, keeping the vent hole in the gas/water valve closed off. The second position blocks the $CO_2$ gas supply to both atmosphere and the gas supply line 240*a* in the endoscope 100, and opens up the gas/water valve 140 to allow lens wash water to pass through to the lens wash supply line 245*a* in the endoscope shaft 100*a* and out the gas/lens wash nozzle 220 at the distal tip 100*c*. Gas (pressure) in the second reservoir 630 is maintained by delivering gas through the second fluid inlet 646. It is contemplated that the one-way valve 658 is in the closed configuration during delivery of the $CO_2$ gas to allow the container 632 to pressurize. In some instances, the one-way valve 658 may be configured to close without user intervention in response to the delivery of $CO_2$ to the second container 632. In some embodiments, the system 600 may include a branched connector (such as, but not limited to a "Y" or "T" connector) at the second fluid inlet 646 to allow either air or $CO_2$ to be used for pressurization or insufflation. It is further contemplated that the second fluid inlet 646 may include a pressure relief valve 662, such as, but not limited to, a 3-way stopcock, a clamp, or a spring-loaded valve, to vent pressure within the second container 632 and/or to block a flow of pressurized gas to the second container 632 during refilling of the second container 632, during procedure change-overs, and/or during equipment change-overs.

It is contemplated that the use of a flexible bag in place of a rigid bottle for the second reservoir 630 may reduce or eliminate the risk of air leaking from bottle and cap connections. This may eliminate the need for clinicians to attempt to remedy the leak by adjusting the cap and bottle assemblies or from discarding a cap and/or bottle if the leak cannot be remedied.

As the pressurized second container 632 is fluidly isolated from the first container 604 when the one-way valve 658 is closed, it is contemplated that the clinician may replace the first reservoir 602 with a new (full) reservoir without losing patient insufflation. Loss of patient insufflation may result in a loss of position of the endoscope 100 within the body. In current one or two bottle systems, it may not be possible to replace the water reservoirs without loss of patient insufflation.

If there is a need to replace the first reservoir 602 with a new full bag, for example when the first reservoir 602 is empty or near empty, the user may hang the new bag near the first reservoir 602 to be replaced. The user may then disengage the spike port adaptor 610 from the port 608*b* and insert the spike port adaptor 610 into a port of the new bag. This may be performed without requiring the clinician to bend or stoop to access the first reservoir 602. The port 608*b* may self-seal to prevent fluid leaks from the first reservoir 602 being replaced. This method of replacing the first reservoir 602 may have a lower risk of introducing contaminants into the systems relative to traditional bottle systems. For example, the change out method described herein may allow the first reservoir 602 to be changed out without having tubing dangling from a cap (as in a bottle system). Further, the system 600 may remain largely closed as the first reservoir 602 is changed out.

Figure 7:
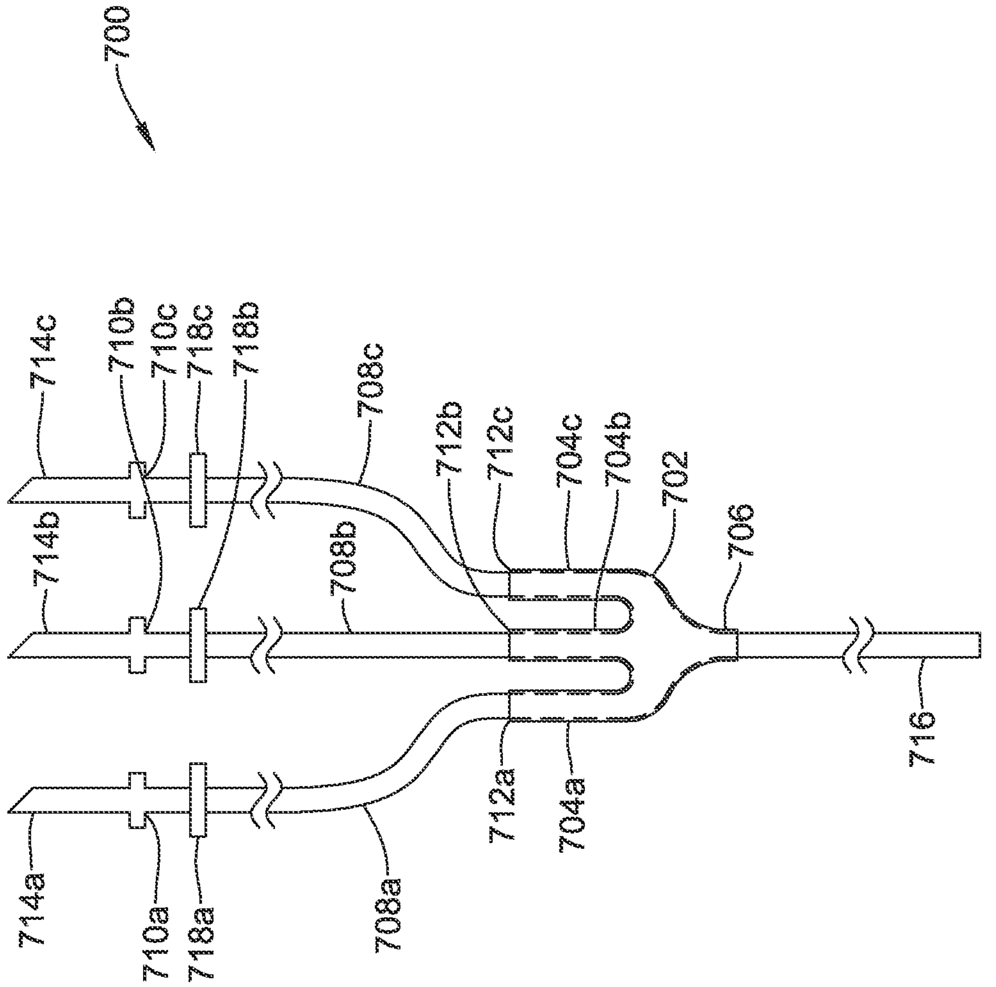
FIG. 7 depicts a schematic manifold assembly for use with a container and tube set.

In some embodiments, it may be desirable to couple multiple reservoirs in parallel to feed the endoscope 100. FIG. 7 depicts a schematic manifold assembly 700 for use with a container and tube set. As used herein, a "manifold" is a structure having two or more openings for making fluid connections. The manifold assembly 700 may include a housing 702 having a plurality of fluid inlets 704*a-c* at a first end of the housing 702 and a fluid outlet 706 at a second opposing end of the housing 702. Each of the fluid inlets 704*a-c* may be in fluid communication with the fluid outlet 706. While the housing 702 is illustrated as including three fluid inlets 704*a-c*, the housing 702 may include fewer than three fluid inlets or more than three fluid inlets, as desired. Further, while the housing 702 is illustrated as including one fluid outlet 706, in some embodiments, the housing 702 may include more than one fluid outlet 706 as desired. For example, the housing 702 may include a first fluid outlet configured to supply fluid to an irrigation circuit and a second fluid outlet configured to supply fluid to a lens wash circuit. However, this is not required. It is contemplated that in other embodiments where it is desired to supply fluid to more than one fluid circuit, a branched connector (similar in form and function to the branched connector 650 described herein) may be used downstream of the manifold assembly 700.

The manifold assembly 700 may further comprise a fluid tube 708*a-c* coupled to each of the fluid inlets 704*a-c* of the housing 702. The fluid tubes 708*a-c* may extend from an inlet end 710*a-c* to an outlet end 712*a-c* coupled to the fluid inlets 704*a-c* of the housing 702. The inlets ends 710*a-c* may each be coupled to or otherwise include a corresponding spike port 714*a-c*. For example, a spike port 714*a-c* may be releasable coupled to the inlets end 710*a-c* of the fluid tube 708*a-c*. Alternatively, the spike port 714*a-c* may be fixedly coupled to or formed as a monolithic structure with the inlet end 710*a-c* of the fluid tube 708*a-c*. The spike ports 714*a-c* may each be configured to be coupled to a different fluid reservoir (such as, but not limited to fluid reservoirs 502, 602). For example, in the illustrated embodiments, the manifold assembly 700 includes three separate spike ports 714*a*, 714*b*, 714*c*. Thus, the manifold assembly 700 may be coupled to up to three fluid reservoirs simultaneously. However, the presence of three spike ports 714*a-c* does not require the manifold assembly 700 to be coupled to three fluid reservoirs or containers simultaneously. In some examples, the manifold assembly 700 may be coupled to a single fluid reservoir or two fluid reservoirs, as desired.

The manifold assembly 700 may further include one or more removable clamps 718*a-c*. The clamps 718*a-c* may be configured to selectively close one or more of the fluid tubes 708*a-c*. For example, in one example, clamps 718*a-b* may be clamped to their respective fluid tubes 708*a-b* to prevent a flow of fluid from the respective reservoir (not explicitly shown) to the housing 702. This may allow fluid to flow from a single reservoir at a time. When the fluidly coupled reservoir is empty, another clamp 718*b* may be removed to allow fluid to flow from a second reservoir. The coupled reservoirs may be used in any order desired and may be used in combination with one or more other reservoirs simultaneously, if desired.

The fluid outlet 706 of the housing 702 may be fluidly coupled to a fluid conduit 716. The fluid conduit 716 may be in fluid communication with an irrigation fluid circuit and/or a lens wash fluid circuit. In some embodiments, the fluid conduit 716 may supply fluid to only one of the irrigation fluid circuit or the lens wash fluid circuit. In other embodiments, the fluid conduit 716 may supply fluid to both the irrigation fluid circuit and the lens wash fluid circuit. For example, the fluid conduit 716 may include a branched connector configured to allow fluid to be directed to both the irrigation fluid circuit and the lens wash fluid circuit, as described with respect to FIG. 6.

Figure 8:
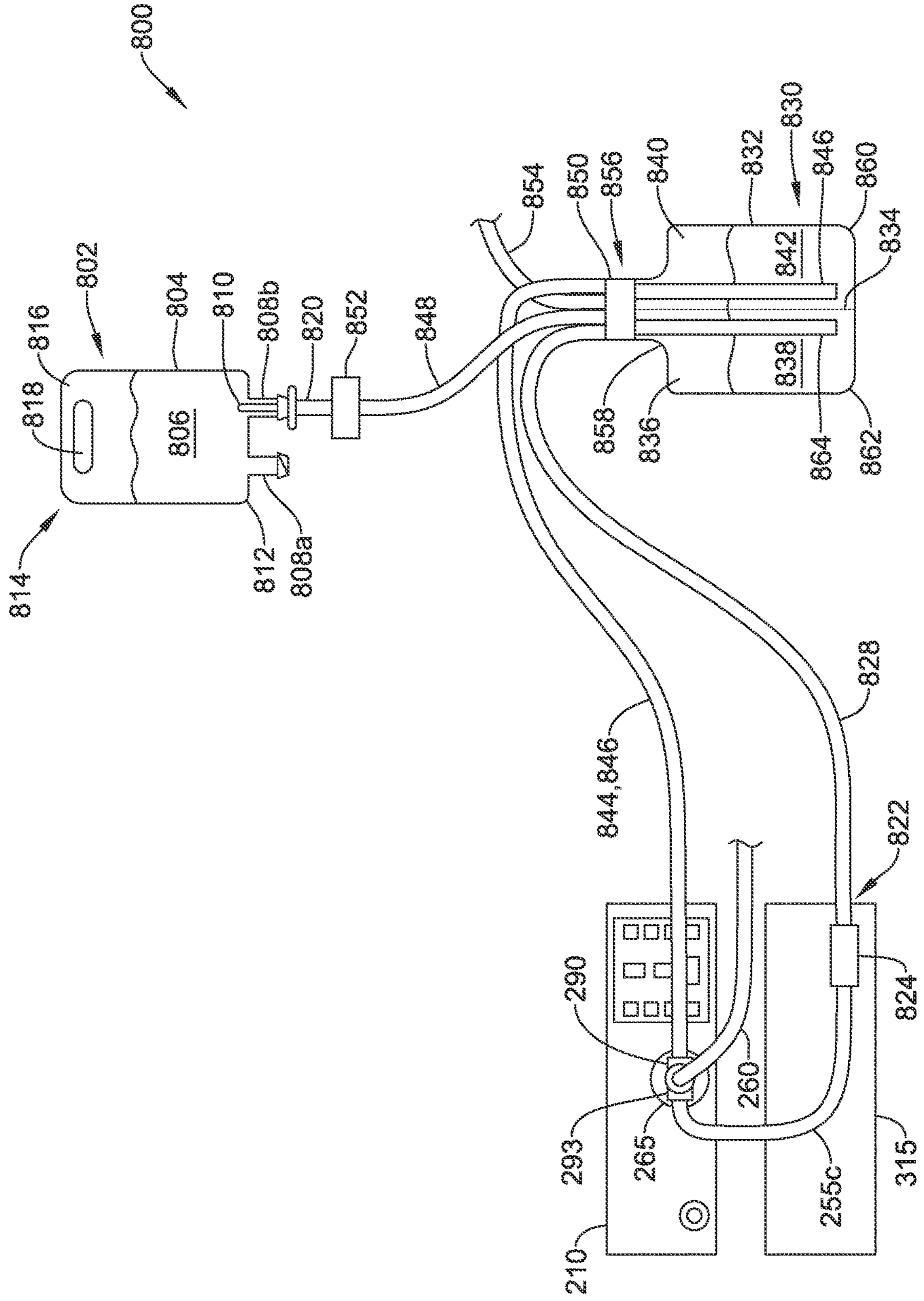
FIG. 8 depicts another illustrative endoscope system having an alternative fluid supply system.

FIG. 8 depicts a schematic view of an illustrative endoscopic system 800 which may reduce the number of water reservoir changes and/or reduce opportunities for contamination during replacement of the water reservoir(s). The system 800 may include a number of advantages over the current bottle system described above. The system 800 may include components similar to the endoscope and endoscope systems described with regard to FIGS. 1-4; however, not all features may be described or shown here.

Generally, the system 800 may include a first reservoir 802 and a second reservoir 830. The first reservoir 802 may be configured to supply fluid to the second reservoir 830 which in turn supplies fluid to the endoscope for both irrigation and lens wash. This may allow a single fluid source to be used to provide fluid for both irrigation and lens wash. While not explicitly shown, the reservoir 802 may include printed lines, numbers, or other visual indicia to allow a user to easily determine how much fluid is left in the reservoir 802.

The first reservoir 802 may include a first container 804 configured to hold a first volume of fluid 806. In the illustrated embodiment, the first container 804 is fluidly coupled to the second reservoir 830. The second reservoir 830 may include a second container 832. The second container 832 may include a partition 834 disposed within an interior thereof to divide the second container 832 into a first sub-chamber 836 configured to hold a second volume of fluid 838 and a second sub-chamber 840 configured to hold a third volume of fluid 842. Generally, the first and second sub-chambers 836, 840 may provide separate fluid sources for lens wash and irrigation. For example, the first sub-chamber 836 may provide fluid for irrigation while the second sub-chamber 840 may provide fluid for lens wash. Having two separate sub-chambers 836, 840 may improve the time required to pressurize the second container 832 to enable lens washing capability. For example, if fluid for both lens wash and irrigation are drawn from the same source or container, the entire container must be pressurized to utilize the lens wash which may cause a lag between the input to lens wash and the function of actually washing the lens.

In the illustrated embodiment, the second container 832 is fluidly coupled to the upstream irrigation supply tubing 828 and is configured to provide fluid for irrigation to the endoscope. Generally, the irrigation supply tubing 828 may be a water or fluid supply line or tube for supplying water or other fluid to an endoscope. Additionally, the second container 832 is fluidly coupled to the gas and lens wash supply tubing 844, 846 and is configured to provide fluid for lens wash to the endoscope. Generally, the lens wash supply tubing 846 may be a water or fluid supply line or tube for supplying water or other fluid to an endoscope. The gas and lens wash supply tubing 844, 846 may be coaxially arranged. For example, the gas supply tubing 844 may define a lumen that is sufficiently large in diameter to encompass a smaller diameter lens wash tubing 846, coaxially received within the gas supply tubing 844, as well as provide air to the water source in an annular space surrounding the lens wash tubing to pressurize the second sub-chamber 840 of the second reservoir 830. The lens wash supply tubing 846 may be configured to exit the lumen defined by the coaxial gas supply tubing 844 in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion 265. In other embodiments, the gas and lens wash supply tubing 844, 846 may be arranged in a side-by-side arrangement.

The first and second containers 804, 832 may be formed from one or more layers of a lightweight, flexible material, such as, but not limited to, low density polyethylene (LDPE), thermoplastic polyurethane (TPU), silicone, polyethylene terephthalate (PET), aluminum, nylon, polyethylene (PE), or combinations thereof, etc. In some embodiments, the first and second containers 804, 832 may be entirely translucent, entirely opaque, or combinations thereof. In some cases, the first and second containers 804, 832 may be a flexible bag analogous to those utilized to deliver intravenous replacement fluid in clinical settings (for example, an intravenous (IV) fluid bag). Such bags may be readily available and familiar to the clinician as they are widely used in various sizes. The volume of the first and second containers 804, 832 may be variable. For example, the volume of the first and/or second container 804, 832 may be 500 milliliters (mL) or greater, 1000 mL or greater, 2000 mL or greater, 3000 mL, 4000 mL or greater, etc. The volume may be less than 500 mL or greater than 4000 mL, as desired. One or both of the first and second reservoirs 802, 830 may be pre-filled (e.g., prior to entering the procedure suite or at the time of manufacturing) with water or other fluid. In some cases, the clinician may select the reservoir(s) 802, 830 from a plurality of differently sized available reservoirs based on the number and/or types of procedures expected for a typical or the specific day. In the illustrated embodiments, the first reservoir 802 may supply fluid to the second reservoir 830. By selecting a first reservoir 802 having a volume large enough to accommodate an entire day of procedures, the need for replacing the sterile fluid source (e.g., the first reservoir 802) may be reduced or eliminated. In some cases, the first reservoir 802 may be used to periodically refill the second reservoir 830. Thus, the volume of the first reservoir 802 may be greater than the volume of the second reservoir 830, although this is not required. It is further contemplated that, in some embodiments, one or both of the first or second reservoirs 802, 830 may be a rigid bottle. For example, in the illustrated embodiment, the first reservoir 802 may be a flexible bag while the second reservoir 830 may be a rigid bottle. The reverse configuration is also contemplated.

It is contemplated that flexible bags may utilize less plastic (or other material) than a bottle designed to hold a similar amount of fluid. Thus, the use of a flexible bag as a fluid reservoir 802, 830 may increase the level of environmental sustainability of the system 800. For example, if the user sets up the system with a 3000 mL (3 liter) bag reservoir 802 and therefore does not need to utilize three individual one liter bottles, a significant reduction of waste may be realized. It is further contemplated that when disposed of or discarded, a flexible bag reservoir may occupy less volume than a bottle capable of holding an equivalent amount of fluid.

The first reservoir 802 may further include one or more ports 808*a*, 808*b*, such as, but not limited to a spike port or a septum port, extending from and in selective fluid communication with an interior of the first container 804. The ports 808*a*, 808*b* may be formed as a monolithic structure with the first container 804. The ports 808*a*, 808*b* may be generally tubular structures with each port 808*a*, 808*b* defining a lumen extending therethrough. The lumens of the ports 808*a*, 808*b* may be configured to selectively fluidly couple the interior of the first container 804 with another component, such as, but not limited to, a fluid supply tube. In some embodiments, the ports 808*a*, 808*b* may be positioned adjacent to a bottom end 812 of the first reservoir 802. However, this is not required. The ports 808*a*, 808*b* may be positioned in other locations, as desired. If the ports 808*a*, 808*b* are positioned at a location other than the bottom end 812 of the first container 804, a dip tube or tube extension may be required to access the fluid at the bottom of the first container 804. In some cases, at least one port 808*b* may be configured to be fluidly coupled to the second container 832 via a fluid or water supply tube 848 while another port 808*a* may be configured to allow the user to add additives to the fluid 806. While the first reservoir 802 is illustrated as including two ports 808*a*, 808*b*, the first reservoir 802 may include one port or more than two ports, as desired.

While not explicitly shown, the ports 808*a*, 808*b* may each include a removable cap or seal configured to form a fluid tight seal with the port 808*a*, 808*b*. The removable cap or seal may help to maintain the sterility of the ports 808*a*, 808*b*. The removable cap or seal may be coupled to a free end of the ports 808*a*, 808*b* using a number of different techniques. For example, the cap or seal may be coupled to the port 808*a*, 808*b* using a threaded engagement, a friction fit, a snap fit, etc. In other instances, the cap or seal may be removed through a twisting motion configured to break the cap or seal from the port 808*a*, 808*b*. Once the cap or seal has been removed, the port 808*a*, 808*b* may be pierced with a spike tip or spike port adaptor 810 that is coupled to a first end of the water supply tube 848. For example, in addition to the removable cap or seal, the port 808*a*, 808*b* may include an internal seal disposed within a lumen of the port 808*a*, 808*b* that may be punctured or pierced by the spike port adaptor 810. The internal seal may be configured to prevent fluid 806 from leaking from the first container 804 prior to the spike port adaptor 810 being inserted into the port 808*a*, 808*b*. In some embodiments, the internal seal may be self-sealing such that upon removal of the spike port adaptor 810 fluid is prevented from leaking from the port 808*a*, 808*b*. The outer surface of the spike port adaptor 810 may form an interference fit with the inner surface of the port 808*a*, 808*b*. The fit and/or coupling between the spike port adaptor 810 and the port 808*a*, 808*b* may be sufficient to remain in place when the water supply tube 848 and/or other tubing sets are coupled to the spike port adaptor 810. It is contemplated that the spike port adaptor 810 may be inserted into one of the ports 808*a*, 808*b* utilizing universally used aseptic techniques such as those used with IV fluid bags. This may help reduce infection risk by maintaining sterile components, not introducing contaminants into the fluid 806, etc. It is further contemplated that additives may be added to the fluid 806 using similar aseptic techniques via one of the ports 808*a*, 808*b*.

The first reservoir 802 may include a handle 816 positioned adjacent to a top portion 814 thereof. The handle 816 may define an opening or through hole 818 for receiving a hand or hook therethrough to carry the first reservoir 802. In some cases, the handle 816 may include an undulating surface configured to provide a more ergonomic grip for the user. It is contemplated that the handle 816 may be formed from a similar material as the first container 804 or a different material, as desired. In some examples, the handle 816 may be formed from polyethylene terephthalate (PET), polypropylene (PP), plasticized polyvinyl chloride (PVC), etc. The handle 816 may allow the first reservoir 802 to be hung from a hook, such as, but not limited to an IV stand. Hanging the first reservoir 802 may allow the first reservoir 802 to be positioned above the level of an endoscope cart which may enable the user to see the fluid 806 level at any time. This may help the clinician avoid running out of fluid during a procedure. Additionally, elevating the reservoir may eliminate the need for the clinician to bend or stoop during setup of the system 800 and/or to change the first reservoir 802. In some cases, head pressure generated from elevating the first reservoir 802 may enable rapid priming of the irrigation circuit (and/or lens wash circuit if so connected) which may save time during setup. It is further contemplated that hanging the first reservoir 802 from a hook or IV stand may allow the first reservoir 802 to be positioned away from expensive capital equipment thus reducing or eliminating the potential for fluid running or flowing inadvertently onto the capital equipment and causing damage or destruction.

The first reservoir 802 may be connected in fluid communication with a lumen of the water supply tube 848. The water supply tube 848 extends from a second end coupled with a cap 850 of the second container 832 to a first end 820 coupled to the spike port adaptor 810. The water supply tube 848 may be configured to selectively fluidly couple the first reservoir 802 with the second reservoir 830. In some cases, the water supply tube 848 may include a flow control mechanism 852, such as, but not limited to a valve, a one-way valve, a clamp, a stopcock, etc., to selectively allow a flow of fluid from the first reservoir 802 to the second reservoir 830. In some embodiments, the flow control mechanism 852 may be positioned within the cap 850 to selectively allow a flow of fluid into the first and/or second sub-chambers 836, 840 and preclude a flow of fluid from the second sub-chamber 840 to the first sub-chamber 836.

The cap 850 may be configured to be releasably coupled to a port or a neck 856 of the second container 832 positioned adjacent to a top portion 858 of the second container 832. The cap 850 may include a plurality of openings or ports to allow a plurality of tubes to be in fluid communication with an interior of the second container 832. The cap 850 may include openings for the water supply tube 848, the gas and lens wash supply tubing 844, 846, the upstream irrigation supply tubing 828, and an alternative gas supply tubing 854. It is contemplated that the cap 850 may be rotated or otherwise articulated between a filling configuration which fluidly couples the water supply tube 848 with the first and/or second sub-chambers 836, 840 to add water or fluid to the first and second sub-chambers 836, 840 and a use configuration which fluidly isolates at least the first and second sub-chambers 836, 840 from the water supply tube 848 to allow for pressurization of the second sub-chamber 840. In some cases, in the use configuration the second sub-chamber 840 may also be fluidly isolated from the first sub-chamber 868. In the filling configuration, the second end of the water supply tube 848 may be configured to be fluid communication with the first and second sub-chambers 836, 840 individually or simultaneously. It is contemplated that the cap 850 need not be physically moved to move between the filling configuration and the use configuration. For example, the flow control mechanism 852 may be opened/closed to move the system between the use configuration and the filling configuration.

The second reservoir 830 may be connected in fluid communication with a gas supply tubing 844 and/or an alternate gas supply tubing 854 and a lens wash supply tubing 846. The gas supply tubing 844 extends from a second end external to the second container 832 through a reservoir opening in the cap 850 adjacent the top portion 858 of the second sub-chamber 840. The gas supply tubing 844 and/or alternate gas supply tubing 854 may terminate within a reservoir gap, at or below the opening, but not extending into the remaining fluid 842 in the second sub-chamber 840. However, in some cases, the gas supply tubing 844 and/or alternate gas supply tubing 854 may extend into the fluid 842. For example, the gas supply tubing 844 and/or alternate gas supply tubing 854 may terminate within the fluid 842 with gas bubbling up through the fluid 842 to pressurize the second sub-chamber 840 (or both the first and second sub-chambers 836, 840). A lumen extends through the gas supply tubing 844 for receiving a flow of air and/or gas therethrough. Similarly, a lumen extends through the alternate gas supply tubing 854 for receiving a flow of gas therethrough. The lumens of the gas supply tubing 844 and/or the alternate gas supply tubing 854 are in operative fluid communication with a top portion of the second sub-chamber 840. The lens wash supply tubing 846 extends from a second end external to the second reservoir 830 through the reservoir opening in the cap 850, terminating in a first end within the remaining fluid 842 at or substantially at a bottom portion 860 of the second container 832. In some embodiments, the water supply tubing 846 may terminate at the opening in the cap 850. A lumen extends through the lens wash supply tubing 846 for receiving a flow of fluid therethrough. The lumen of the lens wash supply 846 is in selective operative fluid communication with the bottom portion of the second sub-chamber 840. In the illustrated embodiment, the gas supply tubing 844 and the water supply tubing 846 may enter the second container 832 through a single or common opening. For example, the gas supply tubing 844 and the lens wash supply tubing 846 may be coaxially arranged. However, this is not required. In some cases, the gas supply tubing 844 and the water supply tubing 846 may extend in a side by side arrangement or may be separately connected to the second container 832 in different locations. The opening in the cap 850 may include a seal or O-ring configured to seal the cap 850 about the tubing 844, 846 in a fluid and pressure tight manner.

In some embodiments, the second reservoir 830 may be connected in fluid communication with a lumen of an irrigation supply tube 828. The irrigation supply tubing 828 extends from a second end region 822 to a first end 864 which extends through an opening and into an interior of the first sub-chamber 836. The second end of the irrigation supply tubing 828 may be external to the second reservoir 830. A lumen extends through the irrigation supply tube 828 for receiving a flow of fluid therethrough. In some cases, the irrigation supply tube 828 may be coupled to a manifold, if so provided. The first end of the irrigation supply tube 828 is in selective fluid communication with the bottom portion 862 of the first sub-chamber 836. The opening in the cap 850 may include a seal or O-ring configured to seal the cap 850 about the tubing 844, 846 in a fluid and pressure tight manner.

The second ends of the gas supply tubing 844 and the lens wash supply tubing 846 may be connected in fluid communication with the endoscope at gas/lens wash connection on the connector portion 265 of the umbilical 260. The gas supply tubing 844 is connected in fluid communication with a gas pump (not explicitly shown) and gas feed line (not explicitly shown), and the lens wash supply tubing 846 is connected in fluid communication with lens wash feed line (not explicitly shown), within connector portion 265. The irrigation tubing 828 is connected in fluid communication with the irrigation supply line (not explicitly shown) via the irrigation pump 315.

When irrigation water is required, fluid is pumped from the first sub-chamber 836 of the second container 832 by operating the irrigation pump 315, such as by depressing a footswitch (not shown). The fluid may flow from the first sub-chamber 836, through the lumen of the upstream irrigation supply tubing 828, through the downstream irrigation supply tubing, through the irrigation connection 293, through the irrigation feed line in the umbilical 260, and down the irrigation supply line in the shaft of the endoscope to the distal tip. While not explicitly shown, the downstream irrigation supply tubing 255*c* may include a loaded check valve or flow control valve positioned in line with the downstream irrigation supply tubing. The flow control valve may prevent the unintentional flow of fluid from the first sub-chamber 836 of the second container 832 to the endoscope. In some cases, the flow control valve may be configured to open when the pressure within the downstream irrigation supply line reaches a predetermined minimum pressure. The flow control valve may also prevent fluid from leaking from the downstream irrigation supply tube when the endoscope is changed between patients.

If there is a need to replace the first reservoir 802 with a new full bag, for example when the first reservoir 802 is empty or near empty, the user may hang the new bag near the first reservoir 802 to be replaced. The user may then disengage the spike port adaptor 810 from the port 808*b* and insert the spike port adaptor 810 into a port of the new bag. This may be performed without requiring the clinician to bend or stoop to access the first reservoir 802. The port 808*b* may self-seal to prevent fluid leaks from the first reservoir 802 being replaced. This method of replacing the first reservoir 802 may have a lower risk of introducing contaminants into the systems relative to traditional bottle systems. For example, the change out method described herein may allow the first reservoir 802 to be changed out without having tubing dangling from a cap (as in a bottle system). Further, the system 800 may remain largely closed as the first reservoir 802 is changed out.

Figure 9:
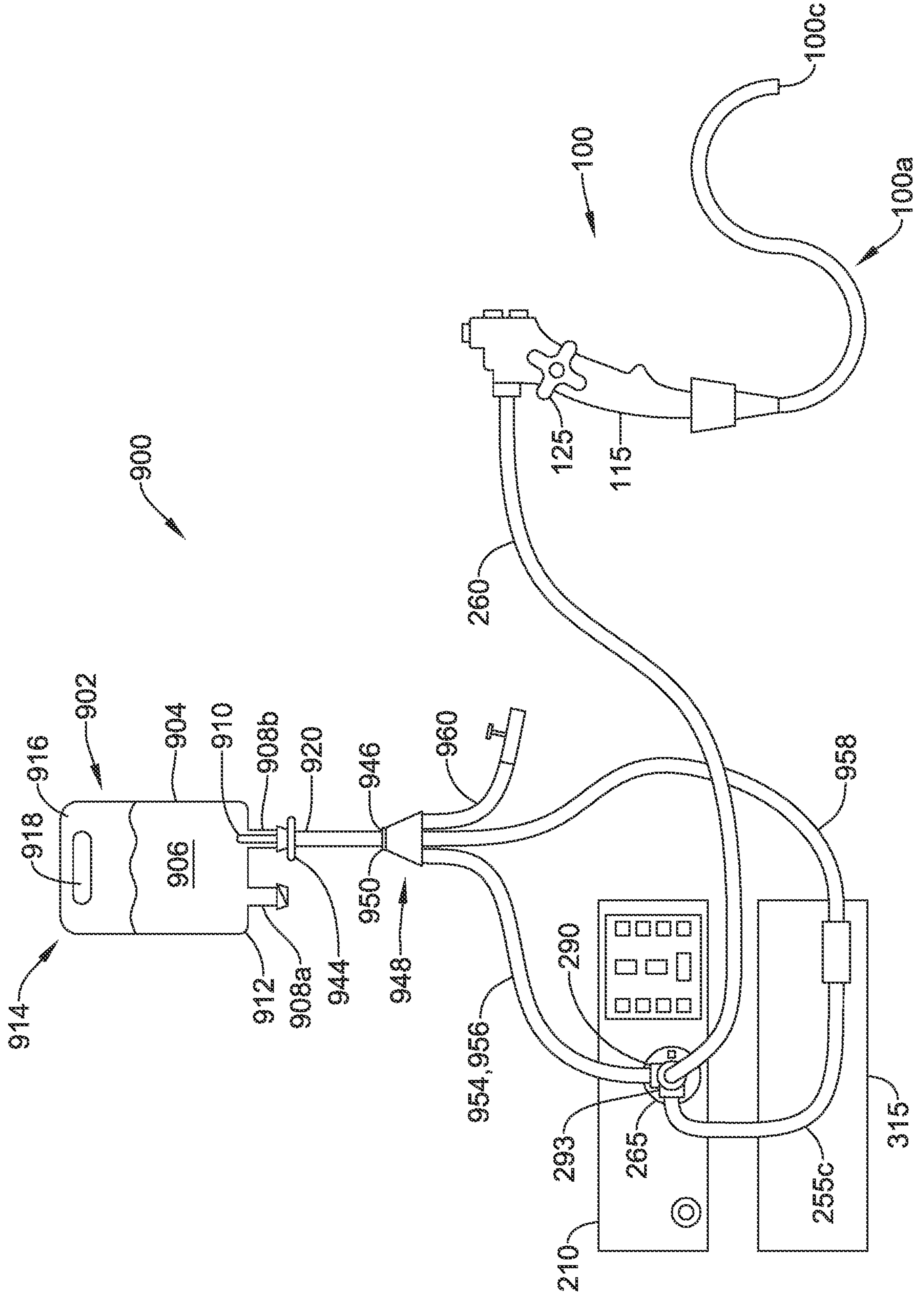
FIG. 9 depicts another illustrative endoscope system having an alternative fluid supply system.

FIG. 9 depicts a schematic view of an illustrative endoscopic system 900 which may reduce the number of water reservoir changes and/or reduce opportunities for contamination during replacement of the water reservoir(s). The system 900 may include components similar to the endoscope and endoscope systems described with regard to FIGS. 1-4; however, not all features may be described or shown here.

The system 900 of FIG. 9 depicts an illustrative fluid reservoir 902 that may include a number of advantages over the current bottle system described above. The reservoir 902 may include a container 904 configured to hold a fluid 906. In the illustrated embodiment, the container 904 is fluidly coupled to a fluid connection tube 920 and is configured to provide fluid for both irrigation and lens wash to the endoscope 100. It is contemplated that providing pressure to the container 904 via the fluid connection tube may eliminate the need for a second reservoir/container. While not explicitly shown, the reservoir 902 may include printed lines, numbers, or other visual indicia to allow a user to easily determine how much fluid is left in the reservoir 902.

The container 904 may be formed from one or more layers of a lightweight, flexible material, such as, but not limited to, low density polyethylene (LDPE), thermoplastic polyurethane (TPU), silicone, polyethylene terephthalate (PET), aluminum, nylon, polyethylene (PE), polyvinyl chloride (PVC), or combinations thereof, etc. In some embodiments, the container 904 may be entirely translucent, entirely opaque, or combinations thereof. In some cases, the container 904 may be a flexible bag analogous to those utilized to deliver intravenous replacement fluid in clinical settings (for example, an intravenous (IV) fluid bag). Such bags may be readily available and familiar to the clinician as they are widely used in various sizes. The volume of the container 904 may be variable. For example, the volume of the container 904 may be 500 milliliters (mL) or greater, 1000 mL or greater, 2000 mL or greater, 3000 mL, 4000 mL or greater, etc. The volume may be less than 500 mL or greater than 4000 mL, as desired. The reservoir 902 may be prefilled (e.g., prior to entering the procedure suite or at the time of manufacturing) with water or other fluid. In some cases, the clinician may select the reservoir 902 from a plurality of differently sized available reservoirs based on the number and/or types of procedures expected for a day. By selecting a reservoir 902 having a volume large enough to accommodate an entire day of procedures, the need for replacing the sterile fluid source (e.g., the reservoir 902) may be reduced or eliminated. It is contemplated that flexible bags may utilize less plastic (or other material) than a bottle designed to hold a similar amount of fluid. Thus, the use of a flexible bag as a fluid reservoir 902 may increase the level of environmental sustainability of the system 900. For example, if the user sets up the system with a 3000 mL (3 liter) bag reservoir 902 and therefore does not need to utilize three individual one liter bottles, a significant reduction of waste may be realized. It is further contemplated that when disposed of or discarded, a flexible bag reservoir may occupy less volume than a bottle capable of holding an equivalent amount of fluid.

The reservoir 902 may further include one or more ports 908*a*, 908*b*, such as, but not limited to a spike port or a septum port, extending from and in selective fluid communication with an interior of the container 904. The ports 908*a*, 908*b* may be formed as a monolithic structure with the first container 904. The ports 908*a*, 908*b* may be generally tubular structures with each port 908*a*, 908*b* defining a lumen extending therethrough. The lumens of the ports 908*a*, 908*b* may be configured to selectively fluidly couple the interior of the container 904 with another component, such as, but not limited to, the fluid connection tube 920. In some embodiments, the ports 908*a*, 908*b* may be positioned adjacent to a bottom end 912 of the reservoir 902. However, this is not required. The ports 908*a*, 908*b* may be positioned in other locations, as desired. If the ports 908*a*, 908*b* are positioned at a location other than the bottom end 912 of the container 904, a dip tube or tube extension may be required to access the fluid at the bottom of the container 904. In some cases, at least one port 908*b* may be configured to be coupled to the fluid connection tube 920 while the other port 908*a* may be configured to allow the user to add additives to the fluid 906. While the reservoir 902 is illustrated as including two ports 908*a*, 908*b*, the reservoir 902 may include one port or more than two ports, as desired.

While not explicitly shown, the ports 908*a*, 908*b* may each include a removable cap or seal configured to form a fluid tight seal with the port 908*a*, 908*b*. The removable cap or seal may help to maintain the sterility of the ports 908*a*, 908*b*. The removable cap or seal may be coupled to a free end of the ports 908*a*, 908*b* using a number of different techniques. For example, the cap or seal may be coupled to the port 908*a*, 908*b* using a threaded engagement, a friction fit, a snap fit, etc. In other instances, the cap or seal may be removed through a twisting motion configured to break the cap or seal from the port 908*a*, 908*b*. Once the cap or seal has been removed, the port 908*a*, 908*b* may be pierced with a spike tip or spike port adaptor 910 that is coupled to the fluid connection tube 920. For example, in addition to the removable cap or seal, the port 908*a*, 908*b* may include an internal seal disposed within a lumen of the port 908*a*, 908*b* that may be punctured or pierced by the spike port adaptor 910. The internal seal may be configured to prevent fluid 906 from leaking from the container 904 prior to the spike port adaptor 910 being inserted into the port 908*a*, 908*b*. In some embodiments, the internal seal may be self-sealing such that upon removal of the spike port adaptor 910 fluid is prevented from leaking from the port 908*a*, 908*b*. The outer surface of the spike port adaptor 910 may form an interference fit with the inner surface of the port 908*a*, 908*b*. The fit and/or coupling between the spike port adaptor 910 and the port 908*a*, 908*b* may be sufficient to remain in place when the fluid connection tube 920, manifold 948, and/or other tubing sets are coupled to the spike port adaptor 910. It is contemplated that the spike port adaptor 910 may be inserted into one of the ports 908*a*, 908*b* utilizing universally used aseptic techniques such as those used with IV fluid bags. This may help reduce infection risk by maintaining sterile components, not introducing contaminants into the fluid 906, etc. It is further contemplated that additives may be added to the fluid 906 using similar aseptic techniques via one of the ports 908*a*, 908*b*.

The reservoir 902 may include a handle 916 positioned adjacent to a top portion 914 thereof. The handle 916 may define an opening or through hole 918 for receiving a hand or hook therethrough to carry the reservoir 902. In some cases, the handle 916 may include an undulating surface configured to provide a more ergonomic grip for the user. It is contemplated that the handle 916 may be formed from a similar material as the container 904 or a different material, as desired. In some examples, the handle 916 may be formed from polyethylene terephthalate (PET), polypropylene (PP), plasticized polyvinyl chloride (PVC), etc. The handle 916 may allow the reservoir 902 to be hung from a hook, such as, but not limited to an IV stand. Hanging the reservoir 902 may allow the reservoir 902 to be positioned above the level of an endoscope cart which may enable the user to see the fluid 906 level at any time. This may help the clinician avoid running out of fluid during a procedure. Additionally, elevating the reservoir may eliminate the need for the clinician to bend or stoop during setup of the system 900 and/or to change the reservoir 902. In some cases, head pressure generated from elevating the reservoir 902 may enable rapid priming of the irrigation circuit (and/or lens wash circuit if so connected) which may save time during setup. It is further contemplated that hanging the reservoir 902 from a hook or IV stand may allow the reservoir 902 to be positioned away from expensive capital equipment thus reducing or eliminating the potential for fluid running or flowing inadvertently onto the capital equipment and causing damage or destruction.

Figure 10A:
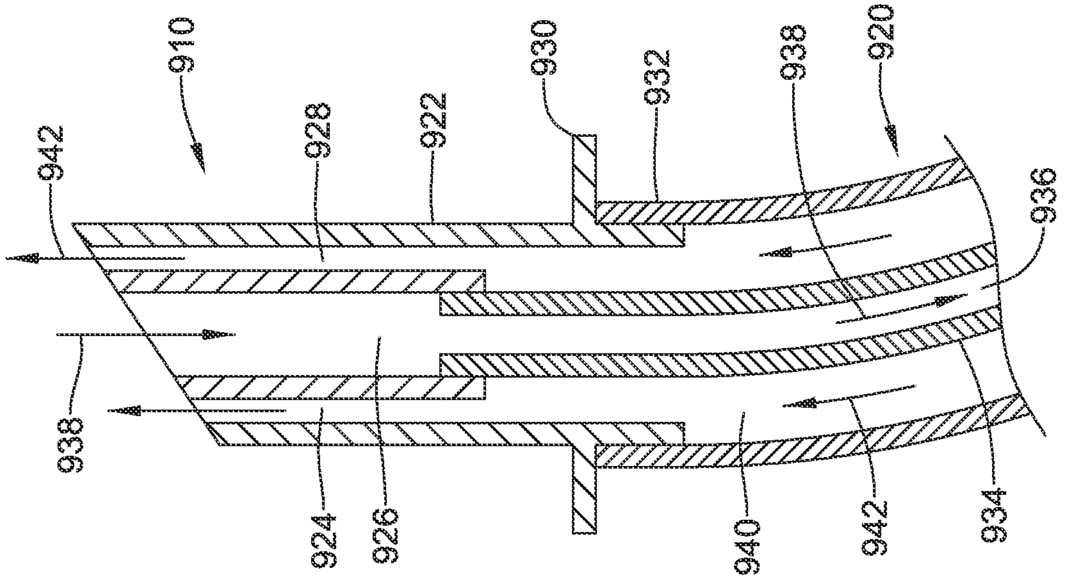
FIG. 10A depicts a schematic cross-sectional view of an illustrative multi-lumen spike port adaptor and fluid connection tube.

The spike port adaptor 910 may include more than one lumen to allow air/gas to be provided to the container 904 for pressurization and for fluid 906 to exit the container 904. FIG. 10A depicts a schematic cross-sectional view of an illustrative multi-lumen spike port adaptor 910 and the fluid connection tube 920. The spike port adaptor 910 may include an outer tubular member 922 and an inner tubular member 924. The inner tubular member 924 may define a lumen 926 extending therethrough. Further, the inner tubular member 924 may be coaxially received within the outer tubular member 922 to define an annular lumen 928 between the outer surface of the inner tubular member 924 and the inner surface of the outer tubular member 922. The spike port adaptor 910 may further include a radially extending shoulder 930 which may provide a mechanical stop between the port 908 of the reservoir 902 and the spike port adaptor 910. In some cases, the radially extending shoulder 930 may provide a gripping or pushing region for the clinician.

The fluid connection tube 920 may be a multi-lumen tube including an outer tube 932 and an inner tube 934. The inner tube 934 may define a lumen 936 configured to be in fluid communication with the lumen 926 of inner tubular member 924 of the spike port adaptor 910. For example, a first end of the inner tube 934 may be coupled to the inner tubular member 924 to define a fluid flow path 938 from the reservoir 902 to the endoscope 100. Further, the inner tube 934 may be coaxially received within the outer tube 932 to define an annular lumen 940 between the outer surface of the inner tube 934 and the inner surface of the outer tube 932. The annular lumen 940 may be in fluid communication with the annular lumen 928 of the spike port adaptor 910. For example, a first end of the outer tube 932 may be coupled to the outer tubular member 922 to define a fluid flow path 942 from exterior to the reservoir 902 to the interior of the reservoir 902.

Returning to FIG. 9, a first end 944 of the fluid connection tube 920 may be coupled to the spike port adaptor 910, as described with respect to FIG. 10A, and a second end 946 of the fluid connection tube 920 may be fluidly coupled to a first end 950 of a manifold 948. As used herein, a “manifold” is a structure having three or more openings for making fluid connections, with the manifold 948 comprising a structure that couples two or more upstream tubes or lumens to three or more downstream tubes or lumens. For example, the manifold 948 may be configured to fluidly couple the annular lumen 940 of the fluid connection tube 920 with the lumen of a gas supply tube 954 and, optionally, with the lumen of an alternative gas supply tube 960. Further, the manifold 948 may be configured to fluidly couple the inner lumen 936 of the fluid connection tube 920 with the lumen of a lens wash supply tube 956 (which may be coaxially disposed within the gas supply tube 954) and the lumen of an irrigation supply tube 958. Generally, the lens wash supply tube 956 and the irrigation supply tube 958 may each be a water or fluid supply line or tube for supplying water or other fluid to an endoscope. In some embodiments, the manifold 948 may include a flow control valve or flow control mechanism disposed therein to control the flow of fluid between the fluid connection tube 920 and the gas supply tube 960, lens wash supply tube 956, and/or the irrigation supply tube 958.

The second end of the irrigation supply tube 958 is configured to be fluidly coupled with an irrigation lumen of the endoscope 100. When irrigation water is required, fluid is pumped from the container 904 by operating the irrigation pump 315, such as by depressing a footswitch (not shown), and flows from the reservoir 902, through the fluid connection tube 920, through the manifold 948, through the irrigation supply tube 958, through the irrigation connection 293, through the irrigation feed line in the umbilical 260, and down the irrigation supply line in the shaft **100*a* of the endoscope to the distal tip 100*c***.

While not explicitly shown, the downstream irrigation supply tubing **255*c* may include a loaded check valve or flow control valve positioned in line with the downstream irrigation supply tubing 255*c*. The flow control valve may prevent the unintentional flow of fluid from the container 904 to the endoscope 100. In some cases, the flow control valve may be configured to open when the pressure within the downstream irrigation supply line 255*c* reaches a predetermined minimum pressure. It is contemplated that the predetermined minimum pressure may be greater than the head pressure created by the height differential between the reservoir 902 and the irrigation pump 315. The flow control valve may also prevent fluid from leaking from the downstream irrigation supply tube when the endoscope 100 is changed between patients. In some embodiments, the irrigation pump 315 may be omitted. For example, the pressure generated by supply air/gas to the reservoir 902 through the gas supply tube 954 and/or the alternative gas supply tube 960 may be sufficient to pump irrigation fluid through the system 900**.

The flow of the air (from the gas supply tube 954) or $CO_2$ (from the alternative gas supply tube 960) through the system 900 may be similar to that described above. For example, in the neutral state, air or $CO_2$ gas flows through the gas supply tube 954 or the alternative gas supply tube 960, through the manifold 948, through the annular lumen 940 of the fluid connection tube 920 and into the container 904, up the gas supply tubing 954 to the connector portion 265, up the gas feed line **240*b* in the umbilical 260, and is vented through the gas/water valve 140 to atmosphere. In the first position, the user closes off the vent hole in the gas/water valve 140, and the air/$CO_2$ gas is flowed through the gas supply tube 954 or the alternative gas supply tube 960, into the container 904, up the gas supply tubing 954 to the connector portion 265, through the gas/water valve 140 to the gas supply line 240*a* in the endoscope shaft 100*a* and out the gas/lens wash nozzle 220 at the distal tip 100*c*. In the second position, the user depresses the valve 140 to the bottom of the valve well 135, keeping the vent hole in the gas/water valve closed off. The second position blocks the $CO_2$ gas supply to both atmosphere and the gas supply line 240*a* in the endoscope 100, and opens up the gas/water valve 140 to allow lens wash water to pass through to the lens wash supply line 245*a* in the endoscope shaft 100*a* and out the gas/lens wash nozzle 220 at the distal tip 100*c*. Gas (pressure) in the reservoir 904 is maintained by delivering gas through the fluid connection tube 920. It is contemplated that the pressure of gas within the annular lumen 940 may prevent water from entering the gas supply tube 954 and/or the alternative gas supply tube 960**.

If there is a need to replace the reservoir 902 with a new full bag, for example when the reservoir 902 is empty or near empty, the user may, optionally, hang the new bag near the reservoir 902 to be replaced. The user may then disengage the spike port adaptor 910 from the port 908*b* and insert the spike port adaptor 910 into a port of the new bag. This may be performed without requiring the clinician to bend or stoop to access the reservoir 902. The port 908*b* may self-seal to prevent fluid leaks from the reservoir 902 as it is being replaced or upon removal of the spike port adaptor 910. This method of replacing the reservoir 902 may have a lower risk of introducing contaminants into the systems relative to traditional bottle systems. For example, the change out method described herein may allow the reservoir 902 to be changed out without having tubing dangling from a cap (as in a bottle system). Further, the system 900 may remain largely closed as the reservoir 902 is changed out.

Figure 10B:
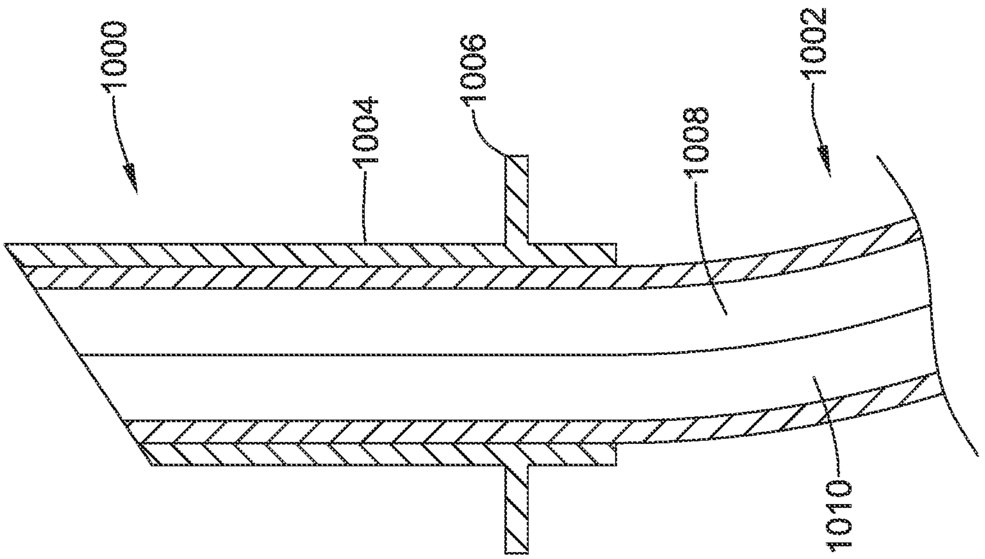
FIG. 10B depicts a schematic cross-sectional view of another illustrative multi-lumen spike port adaptor and fluid connection tube.

FIG. 10B depicts a schematic cross-sectional view of another illustrative multi-lumen spike port adaptor 1000 and the fluid connection tube 1002 that may be used in the system 900 of FIG. 9. The spike port adaptor 1000 may include a tubular member 1004 defining a lumen extending therethrough. The spike port adaptor 1000 may further include a radially extending shoulder 1006 which may provide a mechanical stop between the port 908 of the reservoir 902 and the spike port adaptor 1000. In some cases, the radially extending shoulder 1006 may provide a gripping or pushing region for the clinician.

The fluid connection tube 1002 may be a multi-lumen tube including a first lumen 1008 and a second lumen 1010. The first and second lumens 1008, 1010 may extend side-by-side along a length of the fluid connection tube 1002. It is contemplated that the first and second lumens 1008, 1010 may be lumens of two separate tubes or may be formed as a monolithic extrusion. The fluid connection tube 1002 may extend through the lumen of the tubular member 1004 of the spike port adaptor 1000 to fluidly couple the first and second lumens 1008, 1010 with the reservoir. It is contemplated that air/gas may flow through one of the lumens 1008, 1010 and water or other fluid may flow through the other of the lumens 1008, 1010.

Figure 11:
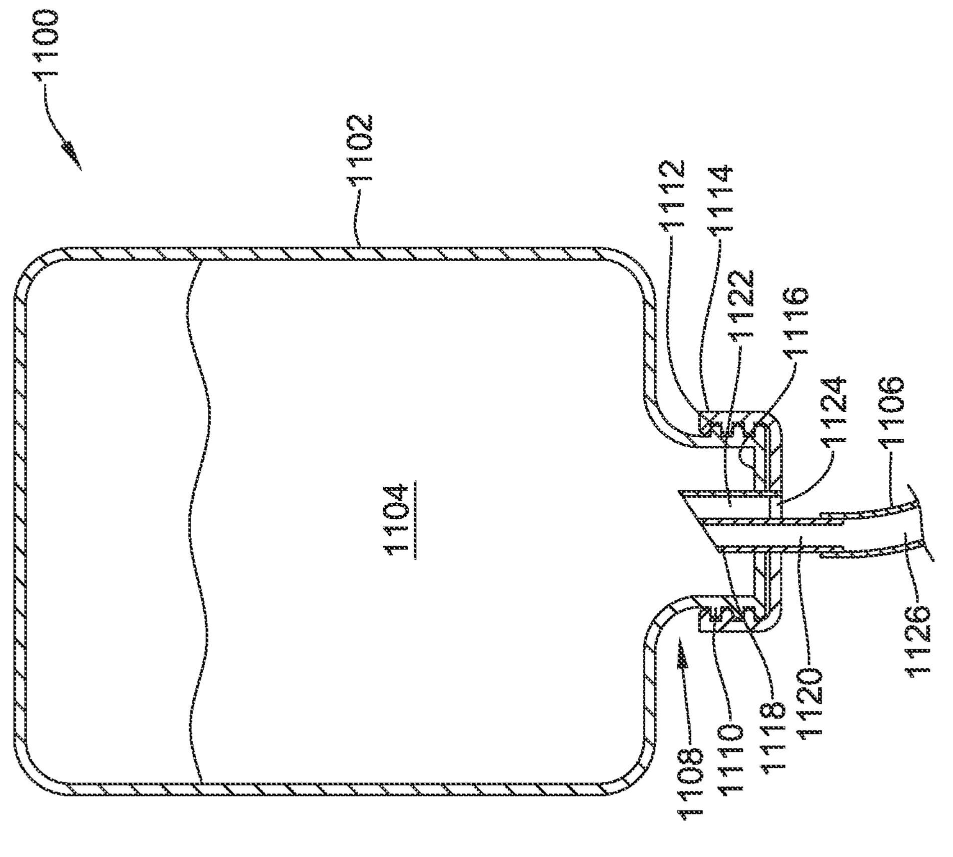
FIG. 11 depicts a schematic cross-sectional view of an illustrative reservoir for use with an endoscope system.

FIG. 11 depicts a schematic cross-sectional view of another illustrative fluid reservoir 1100 that may be used with any of the endoscope systems described herein. The reservoir 1100 may include a container 1102 configured to hold a fluid 1104. In the illustrated embodiment, the container 1102 is fluidly coupled to a fluid or water supply tube 1106 and is configured to provide fluid for irrigation and/or lens wash fluid to the endoscope. For example, the reservoir 1100 may replace reservoir 502 in FIG. 5, reservoir 602 in FIG. 6, reservoir 802 in FIG. 8, and/or reservoir 902 in FIG. 9. In such an instance, the tubing arrangements provided for the reservoirs 502, 602, 802, 902 may be used with the reservoir 1100. It is further contemplated that the reservoir 1100 may replace other reservoirs described herein even if not expressly recited above. While not explicitly shown, the reservoir 1100 may include printed lines, numbers, or other visual indicia to allow a user to easily determine how much fluid is left in the reservoir 1100.

The container 1102 may be a rigid bottle having a reduced diameter neck region 1108. A seal 1116 may be provided across an opening of the neck region 1108 of the container 1102. Prior to use of the container 1102, the seal 1116 may fully cover the opening of the neck region 1108. When the container 1102 is to be used, a cap 1114 including a spike port 1118 may be coupled with the neck region 1108 of the container 1102. The spike port 1118 may be formed as a monolithic structure with a remaining portion of the cap 1114. The neck region 1108 may include a plurality of external threads 1110 configured to threadably engage a plurality of mating internal threads 1112 on the cap 1114. It is contemplated that other coupling mechanisms may be used, as desired, such as, but not limited to, snap fits, friction fits, etc. As the cap 1114 is coupled to the neck region 1108 of the container 1102, the spike port 1118 may pierce or puncture the seal 1116. It is contemplated that the cap 1114 may be coupled with the container 1102 in an upright configuration (e.g., with the opening of neck region 1108 pointing upward). This may help reduce leaks and spills as the cap 1114 and tubing 1106 are assembled. During use, the container 1102 may be inverted (e.g., with the opening of neck region 1108 pointing downward) to place the fluid in fluid communication with the spike port 1118.

The spike port 1118 may define a first lumen 1120 configured to receive a flow of fluid 1104 from the container 1102 when the cap 1114 is coupled with the container 1102 and a second lumen 1122 configured to allow air to enter the interior of the container 1102. For example, a first end of the spike port 1118 may extend into the interior of the container 1102. The second lumen 1122 may extend between a first end configured to be positioned interior of the container 1102 to a second end configured to be open to atmosphere. The second lumen 1122 may include a flow control mechanism 1124 positioned therein. The flow control mechanism 1124 may be positioned anywhere along a length of the lumen 1122 and may be configured to allow air to enter the interior of the container 1102 to prevent a vacuum while preventing fluid 1104 from exiting the container 1102 via the second lumen 1122. In some embodiments, the flow control mechanism 1124 may be hydrophobic filter configured to repel water or a one-way valve.

The fluid supply tube 1106 may be coupled to a second end of the spike port 1118 to fluidly couple a lumen 1126 of the fluid supply tube 1106 with the first lumen 1120 of the spike port 1118. It is contemplated that the fluid supply tube 1106 may supply fluid to the irrigation circuit, as in FIG. 5. In other embodiments, the fluid supply tube 1106 may include a branched connector to supply fluid to the irrigation circuit and a secondary reservoir, as in FIG. 6. In yet other embodiments, the fluid supply tube 1106 may be configured to supply fluid to a secondary reservoir which in turn supplies fluid to the irrigation and lens wash circuits, as in FIG. 8. These are just some examples.

Figure 12:
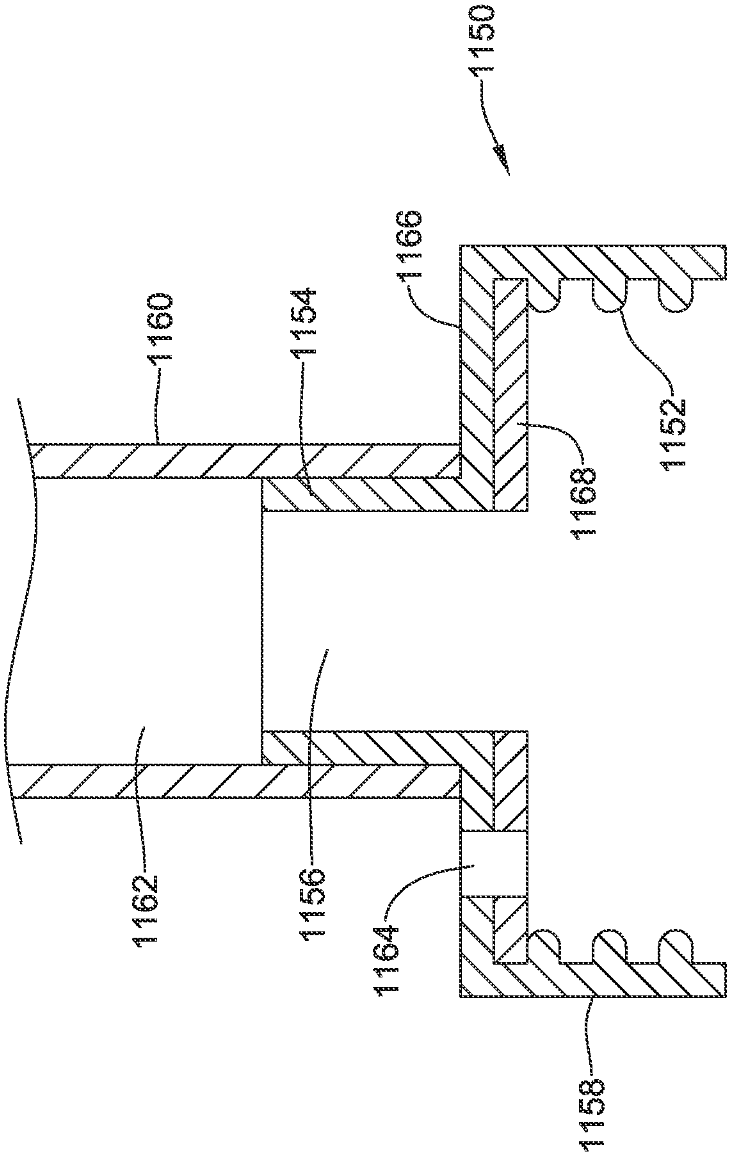
FIG. 12 illustrates a schematic cross-sectional view of an alternative cap that may be used to fluidly couple a water or fluid supply tube with a container.

FIG. 12 depicts a schematic cross-sectional view of an alternative cap 1150 that may be used to fluidly couple a water or fluid supply tube with a rigid bottle (or container), such as, but not limited to, the container 1102 described with respect to FIG. 11. The cap 1150 may be configured to be secured to a reduced diameter neck region (or mouth) of a rigid bottle. The cap 1150 may include a plurality of internal threads 1152 configured to mate with a plurality of external threads on the neck region of the bottle. However, other mechanical engagements may be used, as desired, including, but not limited to, snap fits, friction fits, etc. The cap 1150 may further include a port 1154 defining a lumen 1156. The port 1154 may extend away from a body 1158 of the cap 1150. The lumen 1156 may be configured to fluidly couple an interior of the rigid bottle with a fluid supply tube 1160.

The fluid supply tube 1160 may be coupled to the port 1154 to fluidly couple a lumen 1162 of the fluid supply tube 1160 with the lumen 1156 of the port 1154. It is contemplated that the fluid supply tube 1160 may supply fluid to the irrigation circuit, as in FIG. 5. In other embodiments, the fluid supply tube 1160 may include a branched connector to supply fluid to the irrigation circuit and a secondary reservoir, as in FIG. 6. In yet other embodiments, the fluid supply tube 1160 may be configured to supply fluid to a secondary reservoir which in turn supplies fluid to the irrigation and lens wash circuits, as in FIG. 8. These are just some examples.

The cap 1150 may include a flow control mechanism 1164 extending through an upper wall 1166 thereof. The flow control mechanism may be configured to provide an air/gas flow path from an interior of the container to atmosphere. The flow control mechanism 1164 may be configured to allow air to enter the interior of the container to prevent a vacuum while also preventing fluid from exiting the container via the flow control mechanism 1164. In some embodiments, the flow control mechanism 1164 may be hydrophobic filter configured to repel water or a one-way valve. In another embodiment, the flow control mechanism 1164 may be positioned at the end of a tube or conduit extending from the cap 1150 to the base of the bottle to allow atmospheric air to vent into the bottle more easily (lower vacuum levels). The cap 1150 may further include a sealing member 1168 positioned on an interior surface of the upper wall 1166. The sealing member 1168 may be configured to for a fluid-tight seal between the cap 1150 and the container. The sealing member 1168 may include a gasket, an O-ring, a compressible elastomeric member, etc.

Figure 13:
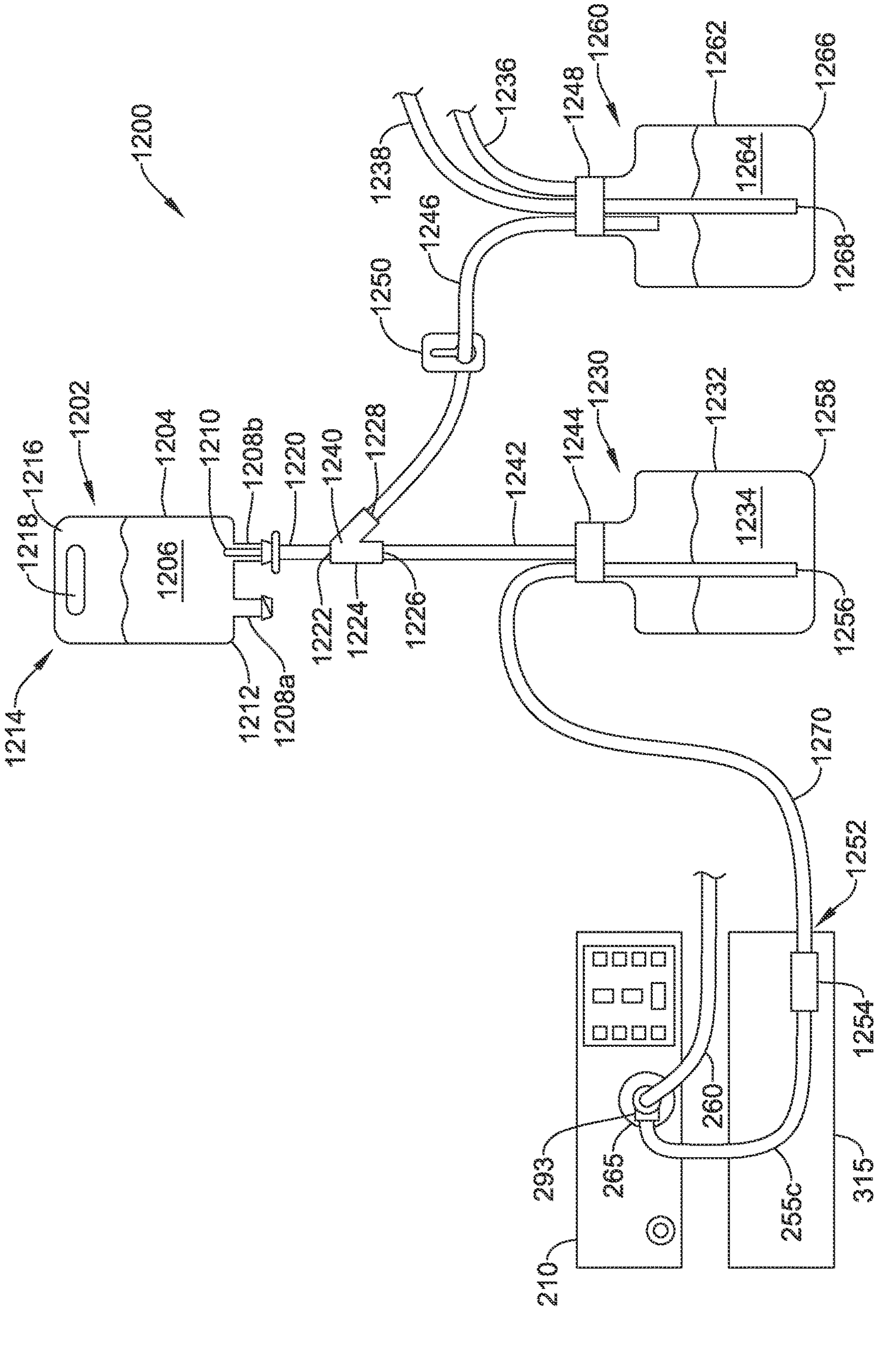
FIG. 13 depicts another illustrative endoscope system having an alternative fluid supply system.

FIG. 13 depicts a schematic view of another illustrative endoscopic system 1200 which may reduce the number of water reservoir changes and/or reduce opportunities for contamination during replacement of the water reservoir(s). The system 1200 may include a number of advantages over the current bottle system described above. The system 1200 may include components similar to the endoscope and endoscope systems described with regard to FIGS. 1-4; however, not all features may be described or shown here.

Generally, the system 1200 may include a first reservoir 1202, a second reservoir 1230, and a third reservoir 1260. The first reservoir 1202 may be configured to supply fluid for both irrigation (e.g., via the second reservoir 1230) and lens wash (e.g., via the third reservoir 1260). This may allow a single fluid source to be used to provide fluid for both irrigation and lens wash. While not explicitly shown, the reservoir 1202 may include printed lines, numbers, or other visual indicia to allow a user to easily determine how much fluid is left in the reservoir 1202.

The first reservoir 1202 may include a first container 1204 configured to hold a first volume of fluid 1206. In the illustrated embodiment, the first container 1204 is fluidly coupled to the second fluid reservoir 1230 and may be selectively fluidly coupled to the third reservoir 1260. The second reservoir 1230 may include a second container 1232 configured to hold a second volume of fluid 1234 and the third reservoir 1260 may include a third container 1262 configured to hold a third volume of fluid 1264. In the illustrated embodiment, the second container 1232 is fluidly coupled to the irrigation supply tubing 1270 and is configured to provide fluid for irrigation. Generally, the irrigation supply tubing 1270 may be a water or fluid supply line or tube for supplying water or other fluid to an endoscope. The third container 1262 may be fluidly coupled to the gas and lens wash supply tubing 1236, 1238 and is configured to provide fluid for lens wash to the endoscope 100. Generally, the lens supply tubing 1238 may be a water or fluid supply line or tube for supplying water or other fluid to an endoscope. In the illustrated embodiment, the gas and lens wash supply tubing 1236, 1238 may be arranged in a side-by-side arrangement. However, in other embodiments, the gas and lens wash supply tubing 1236, 1238 may be coaxially arranged. For example, the gas supply tubing 1236 may define a lumen that is sufficiently large in diameter to encompass a smaller diameter lens wash tubing 1238, coaxially received within the gas supply tubing 1236, as well as provide air to the water source in an annular space surrounding the lens wash tubing 1238 to pressurize the third reservoir 1260. The lens wash supply tubing 1238 may be configured to exit the lumen defined by the coaxial gas supply tubing 1236 in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion 265.

The first container 1204 may be formed from one or more layers of a lightweight, flexible material, such as, but not limited to, low density polyethylene (LDPE), thermoplastic polyurethane (TPU), silicone, polyethylene terephthalate (PET), aluminum, nylon, polyethylene (PE), plasticized polyvinyl chloride (PVC), or combinations thereof, etc. In some embodiments, the first container 1204 may be entirely translucent, entirely opaque, or combinations thereof. In some cases, the first container 1204 may be a flexible bag analogous to those utilized to deliver intravenous replacement fluid in clinical settings (for example, an intravenous (IV) fluid bag). Such bags may be readily available and familiar to the clinician as they are widely used in various sizes. The second and third containers 1232, 1262 may be formed from a rigid bottle. However, it is contemplated that any of the first, second, or third containers 1204, 1232, 1262 may be formed from a flexible bag or a rigid bottle, as desired.

The volume of the first, second, and/or third container 1204, 1232, 1262 may be variable. For example, the volume of the first, second, and/or third container 1204, 1232, 1262 may be 500 milliliters (mL) or greater, 1000 mL or greater, 2000 mL or greater, 3000 mL, 4000 mL or greater, etc. The volume may be less than 500 mL or greater than 4000 mL, as desired. One, two, or all of the first, second, and/or third containers 1204, 1232, 1262 may be pre-filled (e.g., prior to entering the procedure suite or at the time of manufacturing) with water or other fluid. In some cases, the clinician may select the reservoir(s) 1202, 1230, 1260 from a plurality of differently sized available reservoirs based on the number and/or types of procedures expected for a typical or the specific day. In the illustrated embodiments, the first reservoir 1202 may supply fluid to the second reservoir 1230 and the third reservoir 1260. By selecting a first reservoir 1202 having a volume large enough to accommodate an entire day of procedures, the need for replacing the sterile fluid source (e.g., the first reservoir 1202) may be reduced or eliminated. In some cases, the first reservoir 1202 may be used to periodically refill the second reservoir 1230 and/or third reservoir 1260. Thus, the volume of the first reservoir 1202 may be greater than the volume of the second reservoir 1230 and/or third reservoir 1260, although this is not required.

It is contemplated that flexible bags may utilize less plastic (or other material) than a bottle designed to hold a similar amount of fluid. Thus, the use of a flexible bag as a fluid reservoir 1202, 1230, 1260 may increase the level of environmental sustainability of the system 1200. For example, if the user sets up the system with a 3000 mL (3 liter) bag reservoir 1202 and therefore does not need to utilize three individual one liter bottles, a significant reduction of waste may be realized. It is further contemplated that when disposed of or discarded, a flexible bag reservoir may occupy less volume than a bottle capable of holding an equivalent amount of fluid.

The first reservoir 1202 may further include one or more ports 1208*a*, 1208*b*, such as, but not limited to a spike port or a septum port, extending from and in selective fluid communication with an interior of the first container 1204. The ports 1208*a*, 1208*b* may be formed as a monolithic structure with the first container 1204. The ports 1208*a*, 1208*b* may be generally tubular structures with each port 1208*a*, 1208*b* defining a lumen extending therethrough. The lumens of the ports 1208*a*, 1208*b* may be configured to selectively fluidly couple the interior of the first container 1204 with another component, such as, but not limited to, a fluid or water supply tube 1220. In some embodiments, the ports 1208*a*, 1208*b* may be positioned adjacent to a bottom end 1212 of the first reservoir 1202. However, this is not required. The ports 1208*a*, 1208*b* may be positioned in other locations, as desired. If the ports 1208*a*, 1208*b* are positioned at a location other than the bottom end 1212 of the first container 1204, a dip tube or tube extension may be required to access the fluid at the bottom of the first container 1204. In some cases, at least one port 1208*b* may be configured to be coupled to the water supply tube 1220 while another port 1208*a* may be configured to allow the user to add additives to the fluid 1206. While the first reservoir 1202 is illustrated as including two ports 1208*a*, 1208*b*, the first reservoir 1202 may include one port or more than two ports, as desired.

While not explicitly shown, the ports 1208*a*, 1208*b* may each include a removable cap or seal configured to form a fluid tight seal with the port 1208*a*, 1208*b*. The removable cap or seal may help to maintain the sterility of the ports 1208*a*, 1208*b*. The removable cap or seal may be coupled to a free end of the ports 1208*a*, 1208*b* using a number of different techniques. For example, the cap or seal may be coupled to the port 1208*a*, 1208*b* using a threaded engagement, a friction fit, a snap fit, etc. In other instances, the cap or seal may be removed through a twisting motion configured to break the cap or seal from the port 1208*a*, 1208*b*. Once the cap or seal has been removed, the port 1208*a*, 1208*b* may be pierced with a spike tip or spike port adaptor 1210 that is coupled to the water supply tube 1220. For example, in addition to the removable cap or seal, the port 1208*a*, 1208*b* may include an internal seal disposed within a lumen of the port 1208*a*, 1208*b* that may be punctured or pierced by the spike port adaptor 1210. The internal seal may be configured to prevent fluid 1206 from leaking from the first container 1204 prior to the spike port adaptor 1210 being inserted into the port 1208*a*, 1208*b*. In some embodiments, the internal seal may be self-sealing such that upon removal of the spike port adaptor 1210 fluid is prevented from leaking from the port 1208*a*, 1208*b*. The outer surface of the spike port adaptor 1210 may form an interference fit with the inner surface of the port 1208*a*, 1208*b*. The fit and/or coupling between the spike port adaptor 1210 and the port 1208*a*, 1208*b* may be sufficient to remain in place when the water supply tube 1220, branched connector 1224, and/or other tubing sets are coupled to the spike port adaptor 1210. It is contemplated that the spike port adaptor 1210 may be inserted into one of the ports 1208*a*, 1208*b* utilizing universally used aseptic techniques such as those used with IV fluid bags. This may help reduce infection risk by maintaining sterile components, not introducing contaminants into the fluid 1206, etc. It is further contemplated that additives may be added to the fluid 1206 using similar aseptic techniques via one of the ports 1208*a*, 1208*b*.

The first reservoir 1202 may include a handle 1216 positioned adjacent to a top portion 1214 thereof. The handle 1216 may define an opening or through hole 1218 for receiving a hand or hook therethrough to carry the first reservoir 1202. In some cases, the handle 1216 may include an undulating surface configured to provide a more ergonomic grip for the user. It is contemplated that the handle 1216 may be formed from a similar material as the first container 1204 or a different material, as desired. In some examples, the handle 1216 may be formed from polyethylene terephthalate (PET), polypropylene (PP), plasticized polyvinyl chloride (PVC), etc. The handle 1216 may allow the first reservoir 1202 to be hung from a hook, such as, but not limited to an IV stand. Hanging the first reservoir 1202 may allow the first reservoir 1202 to be positioned above the level of an endoscope cart which may enable the user to see the fluid 1206 level at any time. This may help the clinician avoid running out of fluid during a procedure. Additionally, elevating the reservoir may eliminate the need for the clinician to bend or stoop during setup of the system 1200 and/or to change the first reservoir 1202. In some cases, head pressure generated from elevating the first reservoir 1202 may enable rapid priming of the irrigation circuit (and/or lens wash circuit if so connected) which may save time during setup. It is further contemplated that hanging the first reservoir 1202 from a hook or IV stand may allow the first reservoir 1202 to be positioned away from expensive capital equipment thus reducing or eliminating the potential for fluid running or flowing inadvertently onto the capital equipment and causing damage or destruction.

The first reservoir 1202 may be connected in fluid communication with a lumen of the water supply tube 1220. The water supply tube 1220 may extend from a first end coupled to the spike port adaptor 1210 to a second end 1222 coupled to a branched connector 1224. In some embodiments, the branched connector 1224 may be a "Y" connector or a "T" connector having an inlet leg 1240 defining a first fluid inlet, a first outlet leg 1226 defining a first fluid outlet, and a second outlet leg 1228 defining a second fluid outlet. However, it is contemplated that the branched connector 1224 may include more than one fluid inlet and fewer than two or more than two fluid outlets, if so desired.

The inlet leg 1240 of the branched connector 1224 may be coupled to the second end 1222 of the water supply tube 1220 to receive a flow of fluid from the first reservoir 1202. The branched connector 1224 may be configured to divert some of the flow of fluid to the first outlet leg 1226 and some of the flow of fluid to the second outlet leg 1228. The first outlet leg 1226 may be fluidly coupled with a lumen of a second fluid supply tube 1242. The second fluid supply tube 1242 extends from a second end coupled with a cap 1244 of the second container 1232 to a first end coupled with the first outlet leg 1226. The second water supply tube 1242 may be configured to selectively fluidly couple the first reservoir 1202 with the second reservoir 1230. For example, the second water supply tube 1242 may extend through an opening or port in the cap 1244 to allow fluid to pass from the lumen of the second water supply tube 1242 into the interior of the second container 1232. The opening in the cap 1244 may include a seal or O-ring configured to seal the cap 1244 about the tubing 1242 in a fluid and pressure tight manner. In some cases, the second water supply tube 1242 may include a flow control mechanism (not explicitly shown), such as, but not limited to a valve, a one-way valve, a clamp, a stopcock, etc., to selectively allow a flow of fluid from the first reservoir 1202 to the second reservoir 1230.

The second outlet leg 1228 may be fluidly coupled with a lumen of a third fluid supply tube 1246. The third fluid supply tube 1246 extends from a second end coupled with a cap 1248 of the third container 1262 to a first end coupled with the second outlet leg 1228. The third fluid supply tube 1246 may be configured to selectively fluidly couple the first reservoir 1202 with the third reservoir 1260. For example, the third fluid supply tube 1246 may extend through an opening or port in the cap 1248 to allow fluid to pass from the lumen of the third fluid supply tube 1246 into the interior of the third container 1262. The opening in the cap 1248 may include a seal or O-ring configured to seal the cap 1248 about the tubing 1246 in a fluid and pressure tight manner. In some cases, the third fluid supply tube 1246 may include a flow control mechanism 1250, such as, but not limited to a valve, a one-way valve, a clamp, a stopcock, etc., to selectively allow a flow of fluid from the first reservoir 1202 to the third reservoir 1260. It is further contemplated that the flow control mechanism 1250 may prevent a flow of air/gas from the third reservoir 1260 to the first and/or second reservoirs 1202, 1230. It is contemplated that the flow control mechanism 1250 may be opened only when it is desired to add fluid to the third container 1262 from the first container 1204. Fluid may be added to the second container 1232 while the irrigation pump 315 is running or while the irrigation pump 315 is idle, as desired.

The branched connector 1224 may be positioned such that the inlet leg 1240 is upstream of the outlet legs 1226, 1228 relative to a flow of fluid from the first reservoir 1202. In some embodiments, the branched connector 1224 and the spike port 1210 may be molded or formed as a single monolithic structure. It is contemplated that this may reduce connection points in the fluid circuit.

The upstream irrigation supply tube 1270 extends from a second end region 1252 external to the second container 1232 and positioned within a pump head 1254 of the peristaltic irrigation pump 315 to a first end 1256. The first end 1256 of the upstream irrigation supply tube 1270 extends through an opening in the cap 1244 of the second reservoir 1230 and is positioned adjacent to a bottom portion 1258 of the second container 1232. The opening in the cap 1244 may include a seal or O-ring configured to seal the cap 1244 about the tubing 1270 in a fluid and pressure tight manner. The second end of the upstream irrigation supply tube 1270 is configured to be fluidly coupled with an irrigation lumen of the endoscope 100. When irrigation water is required, fluid is pumped from the second container 1232 by operating the irrigation pump 315, such as by depressing a footswitch (not shown), and flows from the second reservoir 1230, through the upstream irrigation supply tubing 1270, through the downstream irrigation supply tubing 255*c*, through the irrigation connection 293, through the irrigation feed line 255*b* in the umbilical 260, and down the irrigation supply line 255*a* in the shaft 100*a* of the endoscope to the distal tip 100*c*. Fluid 1206 from the first reservoir 1202 may be continuously supplied to the second reservoir 1230 as fluid 1234 is pumped from the second reservoir 1230. Alternatively, a flow control mechanism positioned in line with the second fluid supply tube 1242 may be opened to refill the second reservoir 1230 on demand.

The downstream irrigation supply tubing 255*c* may include a loaded check valve or flow control valve (not explicitly shown) positioned in line with the downstream irrigation supply tubing 255*c*. The flow control valve may prevent the unintentional flow of fluid from the first container 1204 to the endoscope 100. In some cases, the flow control valve may be configured to open when the pressure within the downstream irrigation supply line 255*c* reaches a predetermined minimum pressure. The flow control valve may also prevent fluid from leaking from the downstream irrigation supply tube 255*c* when the endoscope 100 is changed between patients.

The gas supply tubing 1236 extends from a second end external to the third container 1262 and through an opening in the cap 1248 thereof. The gas supply tubing 1236 may extend into the interior of the third container 1262 and terminate within a reservoir gap (e.g., above the level of the fluid 1264). However, in some cases, the gas supply tubing 1236 may terminate within the fluid 1264. A lumen extends through the gas supply tubing 1236 for receiving a flow of air and/or gas therethrough. The lumen of the gas supply tubing 1236 may be in operative fluid communication with a top portion of the interior of the third container 1262. The lens wash supply tubing 1238 extends from a second end external to the third reservoir 1260 to a first end 1268 in fluid communication with a bottom portion 1266 of the third container 1262. A lumen extends through the lens wash supply tubing 1238 for receiving a flow of fluid therethrough. In the illustrated embodiment, the gas supply tubing 1236 and the water supply tubing 1238 may couple to the third container 1262 through separate openings in the cap 1248. However, this is not required. In some cases, the gas supply tubing 1236 and the lens wash supply tubing 1238 may be coaxially arranged. The openings in the cap 1248 may include a seal or O-ring configured to seal the cap 1248 about the tubing 1236, 1238 in a fluid and pressure tight manner.

While not explicitly shown, in some embodiments, an alternative gas supply tube may be coupled to an alternative gas supply (e.g., $CO_2$ hospital house gas source) and fluidly coupled to the third reservoir 1260. The alternative gas supply may be used to pressurize the third container 1262 to supply lens wash to the endoscope 100 and/or to provide insufflation.

Fluid 1206 from the first reservoir 1202 may be supplied to the third reservoir 1260 by opening or releasing the flow control mechanism 1250 positioned in line with the third fluid supply tube 1246. In some cases, the pressure within the third reservoir 1260 may need to be relieved prior to allowing fluid to flow from the first reservoir 1202 to the third reservoir 1260. It is contemplated that a pressure relief valve or three-way stopcock may be provided in the gas supply tube 1236 to allow the pressure in the third reservoir 1260 to be relieved. As the pressurized third container 1262 is fluidly isolated from the first container 1204 when the flow control mechanism 1250 is closed, it is contemplated that the clinician may replace the first reservoir 1202 with a new (full) reservoir without losing patient insufflation. Loss of patient insufflation may result in a loss of position of the endoscope 100 within the body. In current one or two bottle systems, it may not be possible to replace the water reservoirs without loss of patient insufflation.

If there is a need to replace the first reservoir 1202 with a new full bag, for example when the first reservoir 1202 is empty or near empty, the user may hang the new bag near the first reservoir 1202 to be replaced. The user may then disengage the spike port adaptor 1210 from the port 1208*b* and insert the spike port adaptor 1210 into a port of the new bag. This may be performed without requiring the clinician to bend or stoop to access the first reservoir 1202. The port 1208*b* may self-seal to prevent fluid leaks from the first reservoir 1202 being replaced. This method of replacing the first reservoir 1202 may have a lower risk of introducing contaminants into the systems relative to traditional bottle systems. For example, the change out method described herein may allow the first reservoir 1202 to be changed out without having tubing dangling from a cap (as in a bottle system). Further, the system 1200 may remain largely closed as the first reservoir 1202 is changed out.

Figure 14:
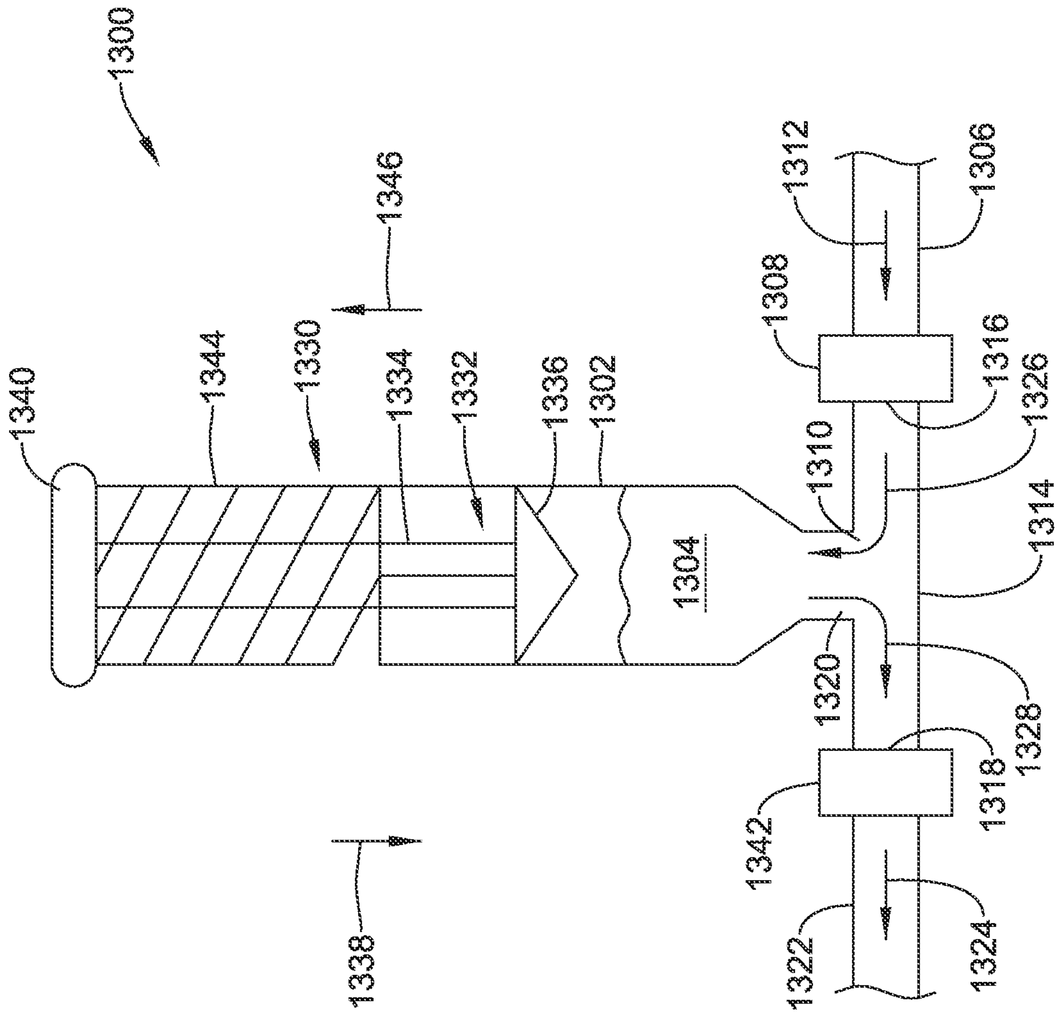
FIG. 14 depicts a schematic container and tube set system for controlling a flow of fluid from a first reservoir to the endoscope.

In some embodiments, it may be desirable to supply irrigation fluid without a dedicated pump or through pressurization of the fluid reservoir. FIG. 14 depicts a schematic container and tube set system 1300 for controlling a flow of fluid from a first reservoir (not explicitly shown) to the endoscope. The illustrated container and tube set may include a container 1302 configured to store a volume of fluid 1304. In the illustrated embodiment, the container 1302 may be relatively rigid. However, in other embodiments, the container 1302 may be semi-flexible, as will be described in more detail herein.

A three-way port 1314 may be coupled to an opening 1310 of the container 1302. It is contemplated that the three-way port 1314 may be a separate structure coupled to the container 1302 or may be formed as a unitary structure with the container 1302. The three-way port 1314 may include a first fluid inlet 1316, a first fluid outlet 1318, and a combination fluid inlet/outlet 1320. The combination fluid inlet/outlet 1320 may be fluidly coupled with the opening 1310 of the container 1302. The first fluid inlet 1316 may be coupled to a first water supply line 1306 via a first flow control mechanism 1308, such as, but not limited to, a one-way valve. The first flow control mechanism 1308 may be positioned in line with the first water supply line 1306. The first flow control mechanism 1308 may be configured to allow fluid within the first fluid line 1306 to flow towards the container 1302, as shown at arrows 1312, 1326, but prevent fluid from flowing from the container 1302 to the first fluid supply line 1306. The first fluid outlet 1318 may be coupled to a second water supply line 1322 via a second flow control mechanism 1342, such as, but not limited to, a one-way valve. The second flow control mechanism 1342 may be positioned in line with the second water supply line 1322. The second flow control mechanism 1342 may be configured to allow fluid within the container 1302 to flow out of the container 1302, as shown at arrows 1324, 1328, but prevent fluid from back flowing into the container 1302 from the second fluid supply line 1322.

The container 1302 may further include a pressure control device 1330 in communication with an interior thereof. In some embodiments, the pressure control device 1330 may be a syringe 1332 including a plunger 1334 and a sealing tip 1336. A biasing mechanism 1344, such as, but not limited to, a spring, may be positioned about the plunger 1334 and between a first end of the container 1302 and an actuation member 1340. The biasing mechanism 1344 may be configured to bias the syringe 1332 towards a top dead center position (e.g., the sealing tip 1336 moves away from the opening 1310 of the container 1302). The sealing tip 1336 may provide a pressure tight seal between the pressure control device 1330 and an inner wall of the container 1302. The pressure control device 1330 may be axially displaced within the container 1302 towards the opening 1310, as shown at arrow 1338, using pressure applied to the actuation member 1340 with the hand or foot. For example, the container and tube set system 1300 may be placed on the floor such that the clinician may use a foot to actuate the pressure control device 1330. However, this is not required. The container and tube set system 1300 may be positioned at other convenient locations relative to the endoscope, as desired. In other embodiments, the pressure control device 1330 may be a pneumatic plunger which may be axially displaced within the container 1302 using air pressure. In yet another embodiment, the pressure control device 1330 may be a solenoid. In a further example, the pressure control device 1330 may be formed as a part of the container 1302. For example, the container 1302 may be formed from a semi-flexible material and include a plurality of bellows which allows the container 1302 to be compressed and released.

The pressure control device 1330 is configured to be actuated to draw fluid 1304 into the interior of the container 1302 and actuated again to push fluid 1304 out of the interior of the container 1302. For example, a clinician may depress the actuation member, 1340, such as, but not limited to, a foot pedal, to move the sealing tip 1336 towards the opening 1310 of the container 1302, as shown at arrow 1338. As the sealing tip 1336 forms a pressure tight seal with the inner wall of container 1302, movement of the pressure control device 1330 expels fluid from the interior of the container 1302, through the first fluid outlet 1318, through the second one-way valve 1342 and into the second fluid supply line 1322, as shown at arrows 1328, 1324. Upon release of the actuation member 1340, the biasing mechanism biases or moves the pressure control device 1330 upwards or away from the opening 1310 of the container 1302, as shown at arrow 1346. As the sealing tip 1336 moves away from the opening 1310, fluid is pulled into the interior of the container 1302 from the first fluid supply line 1036 via the first one-way valve 1308 and the first fluid inlet 1316, as shown at arrows 1312, 1326.

In use, to fill the container 1302 with water, the clinician depresses the actuation member 1340 to drive the sealing tip 1336 towards the bottom of the container 1302 (e.g., towards the opening 1310), as shown at arrow 1338. Once the actuation member 1340 is released, the biasing mechanism 1344 pushes the actuation member 1340, and thus the pressure control device 1330 upwards, as shown at arrow 1346, filling the container 1302 with fluid from the first fluid supply line 1306. The first fluid supply line 1306 may be in fluid communication with a first reservoir, such as a fluid filled flexible bag or rigid container, to supply fluid to the container 1302. When the clinician depresses the actuation member 1340 again, fluid is expelled from the container 1302, through the second one-way valve 1342, and into the second fluid supply line 1322. The second fluid supply line 1322 may be in fluid communication with an irrigation supply line and/or lens wash supply line of the endoscope to provide irrigation and/or lens wash fluid. It is contemplated that the clinician may control a volume of fluid delivered to the endoscope by adjusting how far the actuation member 1340 is depressed. The actuation member 1340 may be depressed and released as many times as desired. Fluid may be supplied to the endoscope using the system 1300 until the first reservoir is depleted of fluid. It is contemplated that the first reservoir may be positioned above the system 1300 to allow fluid to gravity feed into the first fluid supply line 1306.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. A container and tube set arranged and configured to couple to an endoscope for use in an endoscopic procedure, the container and tube set comprising:

a first container configured to contain a fluid, the first container having a port in fluid communication with a bottom portion thereof;

a first water supply tube including a first end, a second end, and a first lumen extending therethrough, wherein the first lumen is in fluid communication with the first container and the second end of the first water supply tube is positioned external to the first container;

a branched connector positioned in line with the first water supply tube between the first and second ends thereof, the branched connector including a first fluid inlet, a first fluid outlet, and a second fluid outlet, a portion of the first lumen of the first water supply tube extending between the first fluid inlet and the first fluid outlet;

a second container configured to contain the fluid, the second container having a second fluid inlet in selective fluid communication with the second fluid outlet of the branched connector;

a second water supply tube including a first end, a second end, and a second lumen extending therethrough, wherein the second lumen is in selective fluid communication with the bottom portion of the second container and the second end of the second water supply tube is positioned external to the second container; and a first gas supply tube including a first end, a second end, and a third lumen extending therethrough, wherein the third lumen is in operative fluid communication with the second container and the second end of the first gas supply tube is positioned external to the second container.

2. The container and tube set of claim 1, wherein the first and second containers each comprise a collapsible bag.

3. The container and tube set of claim 1, wherein the first and second containers each comprise a rigid bottle.

4. The container and tube set of claim 3, wherein the first container comprises a vented cap.

5. The container and tube set of claim 1, further comprising a valve positioned between the second fluid outlet of the branched connector and the second fluid inlet of the second container.

6. The container and tube set of claim 5, wherein the valve is configured to selectively fluidly couple the first container with the second container.

7. The container and tube set of claim 5, wherein the valve is configured to preclude a flow of fluid from the second container to the first container.

8. The container and tube set of claim 1, further comprising a second gas supply tube including a first end, a second end, and a fourth lumen extending therethrough, wherein the fourth lumen is in operative fluid communication with the second container and the second end of the first gas supply tube is positioned external to the second container.

9. The container and tube set of claim 1, wherein the first ends of the second water supply tube and the first gas supply tube are fluidly coupled to a bottom portion of the second container.

10. The container and tube set of claim 1, further comprising a flow control valve in line with the first water supply tube adjacent the second end thereof.

11. The container and tube set of claim 1, further comprising a manifold coupled to the first end of the first water supply tube.

12. The container and tube set of claim 11, wherein the manifold includes a plurality of fluid inlets each configured to be coupled to a fluid container and a third fluid outlet, wherein at least one of the plurality of fluid inlets is fluidly coupled with the first container and the third fluid outlet is fluidly coupled to the first water supply tube.

13. A container and tube set arranged and configured to couple to an endoscope for use in an endoscopic procedure, the container and tube set comprising:

a first container configured to contain a fluid, the first container having a port in fluid communication with a bottom portion thereof;

a first water supply tube including a first end, a second end, and a first lumen extending therethrough, wherein the first lumen is in fluid communication with the first container and the second end of the first water supply tube is positioned external to the first container;

a branched connector positioned in line with first water supply tube between the first and second ends thereof, the branched connector including a first fluid inlet, a first fluid outlet, and a second fluid outlet, a portion of the first lumen of the first water supply tube extending between the first fluid inlet and the first fluid outlet;

a second container configured to contain the fluid, the second container having a second fluid inlet in selective fluid communication with the second fluid outlet of the branched connector;

a one-way valve positioned between the second fluid outlet of the branched connector and the second fluid inlet of the second container;

a second water supply tube including a first end, a second end, and a second lumen extending therethrough, wherein the second lumen is in selective fluid communication with the bottom portion of the second container and the second end of the second water supply tube is positioned external to the container;

a first gas supply tube including a first end, a second end, and a third lumen extending therethrough, wherein the third lumen is in operative fluid communication with the second container and the second end of the first gas supply tube is positioned external to the second container; and a second gas supply tube including a first end, a second end, and a fourth lumen extending therethrough, wherein the fourth lumen is in operative fluid communication with the second container and the second end of the first gas supply tube is positioned external to the second container.

14. The container and tube set of claim 13, further comprising a manifold coupled to the first end of the first water supply tube.

15. The container and tube set of claim 14, wherein the manifold includes a plurality of fluid inlets each configured to be coupled to a fluid container and a third fluid outlet, wherein at least one of the plurality of fluid inlets is fluidly coupled with the first container and the third fluid outlet is fluidly coupled to the first water supply tube.

16. The container and tube set of claim 13, wherein the first and second containers each comprise a collapsible bag.

* * * * *